United States Patent
Maruyama et al.

(10) Patent No.: US 10,077,229 B2
(45) Date of Patent: Sep. 18, 2018

(54) ETHER-CONTAINING MONOESTER COMPOUND AND USE THEREOF

(71) Applicant: Moresco Corporation, Kobe-Shi, Hyogo (JP)

(72) Inventors: Shingo Maruyama, Kobe (JP); Yoshifumi Nakacho, Kobe (JP)

(73) Assignee: MORESCO CORPORATION, Kobe-Shi, Hyogo (JP)

( * ) Notice: Subject to any disclaimer, the term of this patent is extended or adjusted under 35 U.S.C. 154(b) by 0 days.

(21) Appl. No.: 14/913,170

(22) PCT Filed: Jul. 11, 2014

(86) PCT No.: PCT/JP2014/068618
§ 371 (c)(1),
(2) Date: Feb. 19, 2016

(87) PCT Pub. No.: WO2015/040937
PCT Pub. Date: Mar. 26, 2015

(65) Prior Publication Data
US 2016/0200998 A1    Jul. 14, 2016

(30) Foreign Application Priority Data
Sep. 20, 2013    (JP) ................................. 2013-194735

(51) Int. Cl.
| | |
|---|---|
| *C07C 69/708* | (2006.01) |
| *F16C 32/06* | (2006.01) |
| *F16C 33/04* | (2006.01) |
| *F16C 33/66* | (2006.01) |
| *C10M 105/34* | (2006.01) |
| *C10M 129/70* | (2006.01) |
| *F16C 33/10* | (2006.01) |

(52) U.S. Cl.
CPC ......... *C07C 69/708* (2013.01); *C10M 105/34* (2013.01); *C10M 129/70* (2013.01); *F16C 32/06* (2013.01); *F16C 33/04* (2013.01); *F16C 33/6633* (2013.01); *F16C 33/6696* (2013.01); *C10M 2207/281* (2013.01); *C10M 2207/2815* (2013.01); *C10M 2215/064* (2013.01); *C10N 2220/021* (2013.01); *C10N 2220/022* (2013.01); *C10N 2230/06* (2013.01); *C10N 2230/08* (2013.01); *C10N 2230/10* (2013.01); *C10N 2240/02* (2013.01); *C10N 2240/20* (2013.01); *C10N 2240/203* (2013.01); *C10N 2240/204* (2013.01); *C10N 2240/30* (2013.01); *C10N 2250/10* (2013.01); *F16C 33/109* (2013.01)

(58) Field of Classification Search
CPC . C07C 69/708; C10M 129/70; C10M 105/34; C10M 2207/2815; C10M 2215/064; C10M 2207/281; F16C 33/04; F16C 32/06; F16C 33/6633; F16C 33/6696; F16C 33/109; C10N 2240/204; C10N 2230/08; C10N 2240/20; C10N 2220/021; C10N 2230/06; C10N 2240/30; C10N 2240/02; C10N 2240/203; C10N 2220/022; C10N 2230/10; C10N 2250/10
See application file for complete search history.

(56) References Cited

U.S. PATENT DOCUMENTS

| | | | |
|---|---|---|---|
| 2,799,656 A | 7/1957 | Mikeska et al. | |
| 2,936,856 A | 5/1960 | Braunwarth et al. | |
| 4,766,153 A * | 8/1988 | Casciani | A61K 8/39 510/158 |
| 5,503,762 A | 4/1996 | Bongardt et al. | |
| 5,759,968 A | 6/1998 | Furutani et al. | |
| 5,962,117 A * | 10/1999 | Furutani | C10M 105/60 428/421 |

FOREIGN PATENT DOCUMENTS

| | | |
|---|---|---|
| CN | 101426879 A | 5/2009 |
| EP | 2009074 A1 | 12/2008 |
| JP | H07-224289 A | 8/1995 |
| JP | H07-508783 A | 9/1995 |
| JP | H09-132787 A | 5/1997 |
| JP | 2006-096849 A | 4/2006 |
| JP | 2012-056873 A | 3/2012 |
| JP | 2012-106948 A | 6/2012 |
| JP | 5-331474 B2 | 10/2013 |
| WO | WO-93/017172 A1 | 9/1993 |
| WO | WO-2006/059687 A1 | 6/2006 |

OTHER PUBLICATIONS

Masaki Kumagai et al. "Thermal properties of oxaalkanoic acid oxaalkyl esters", Oct. 11, 2011.
International Search Report for PCT/JP2014/068618, dated Sep. 30, 2014.
Office Action issued in corresponding Chinese patent application No. 201480046110.X.
English Translation of International Preliminary Report on Patentability dated Mar. 31, 2016 for PCT/JP2014/068618.

* cited by examiner

*Primary Examiner* — Taiwo Oladapo
(74) *Attorney, Agent, or Firm* — Harness, Dickey and Pierce, P.L.C.

(57) ABSTRACT

A compound of the present invention is represented by the general formula (1) and has a 40° C. kinetic viscosity (v) that satisfies 4 mm²/s≤v≤30 mm²/s,

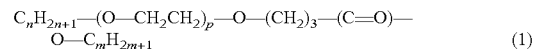

$$C_nH_{2n+1}-(O-CH_2CH_2)_p-O-(CH_2)_3-(C=O)-O-C_mH_{2m+1} \quad (1)$$

(where O represents an oxygen atom, C represents a carbon atom, H represents a hydrogen atom, m is an integer of 1 to 18, n is an integer of 1 to 12, p is an integer of 1 to 3, and 2≤n+m≤30 is satisfied). The present invention provides (i) a lubricant excellent in energy-saving, heat resistance, and low-temperature fluidity and (ii) use of the lubricant.

15 Claims, No Drawings

ETHER-CONTAINING MONOESTER COMPOUND AND USE THEREOF

PRIORITY STATEMENT

This application is a national stage application under 35 U.S.C. § 371 of PCT International Application No. PCT/JP2014/068618 which has an International filing date of 11 Jul. 2014, which claims priority under 35 U.S.C. § 119 to Japanese Application No. 2013-194735 filed 20 Sep. 2013. The contents of each application recited above are incorporated herein by reference in their entirety.

TECHNICAL FIELD

The present invention relates to (i) an ether-containing monoester compound which is low in viscosity and excellent in heat resistance and low-temperature fluidity, (ii) a lubricant containing the ether-containing monoester compound, and (iii) use of the ether-containing monoester compound and the lubricant.

BACKGROUND ART

As the industrial field has diversified and advanced in recent years, electronic devices such as audio-visual devices, servers and personal computers have been dramatically reduced in size and weight, increased in memory capacity, and increased in information processing speed. Such electronic devices employ various rotating devices, for example, rotating devices for driving magnetic disks and optical discs such as FD, MO, zip, mini disc, compact disc (CD), DVD and hard disk. The reduction in size and weight of and the increase in memory capacity and information processing speed of these electronic devices are greatly attributed to improvement in bearings essential to the rotating devices. In particular, a fluid dynamic bearing, which is made up of a sleeve member and a shaft member facing each other via a lubricant, is not only suitable to reduce the size and weight of an electronic device but also excellent in silence, economical efficiency and the like, because the fluid dynamic bearing does not have a ball bearing. Thanks to these characteristics, the fluid dynamic bearing has been increasingly used in servers, personal computers, audio devices, visual devices, car navigation systems and the like.

Examples of properties which a lubricant should have include (i) excellent energy-saving (i.e., low viscosity), (ii) excellent heat resistance (i.e., oxidation resistance, volatility resistance, and a small change in viscosity due to an increase in temperature), (iii) excellent fluidity at low temperature (excellent low-temperature fluidity), and like properties, in addition to basic properties (e.g., lubricity, stability against deterioration (lifetime), property of preventing sludge from being generated, anti-wearing property, anti-corrosion property and like properties).

For example, in a case where, in electronic devices such as audio-visual devices, servers and personal computers, a bearing is rotated at high speed for high-speed processing of large-volume information, load on the bearing increases, thereby remarkably increasing an internal temperature of the bearing. Because of this, great importance is placed on heat resistance of properties which a bearing lubricant should have.

These electronic devices have been increasingly required not only to be capable of high-speed processing of large-volume information but also to be further reduced in size. These electronic devices can be reduced in size by increasing the lifetime of or reducing the capacity of a battery contained in these electronic devices. These electronic devices therefore have been still strongly required to be more energy-saving. In order for the electronic devices to be more energy-saving, one way is to use a lubricant having a low viscosity as a bearing lubricant.

Moreover, as the foregoing information processing devices have been popularized, there have been an increasing number of cases where they are used under harsher environments. In particular, car navigation systems etc. which are mounted on a vehicle are required, considering the environment in which the vehicle is used, to be resistant to a wide range of temperatures including those of cold climates and hot sunlight. Therefore, in a case where a bearing lubricant is used in on-vehicle devices, it is required to be usable without any problems in a wide range of temperatures, for example, from −20° C. to 120° C. To this end, there is a demand for a lubricant that keeps a low viscosity even at low temperatures and suffers little evaporation loss even at high temperatures.

In a further case where a lubricant is used as a lubrication oil of a freezer (freezer oil), the lubricant is required to be (iv) excellent in compatibility with or solubility to a coolant, in addition to the above properties (i) through (iii).

Synthetic hydrocarbon oils and organic acid esters are used as traditional lubricants. For example, Patent Literature 1 discloses a hindered ester synthetic lubrication base oil.

Patent Literature 2 discloses a freezer working fluid composition that contains a specific ester whose iodine number is not more than 1 (1 g/100 g).

Patent Literature 3 discloses a base oil made of (i) a specific composite ester and (ii) dicarboxylic acid ester of adipic acid.

Patent Literature 4 discloses a lubrication base oil composition that contains a specific dibasic acid ester compound and polyester.

Patent Literature 5 discloses that a specific alkoxy ester is suitable for a lubricant.

CITATION LIST

Patent Literature

Patent Literature 1: Japanese Patent Application Publication, Tokukaihei, No. 7-224289 (Publication Date: Aug. 22, 1995)

Patent Literature 2: Japanese Patent Application Publication, Tokukaihei, No. 5-331474 (Publication Date: Dec. 14, 1993)

Patent Literature 3: Japanese Patent Application Publication (Japanese Translation of PCT International Application), Tokuhyohei, No. 7-508783 (Publication Date: Sep. 28, 1995)

Patent Literature 4: Japanese Patent Application Publication, Tokukai, No. 2012-56873 (Publication Date: Mar. 22, 2012)

Patent Literature 5: U.S. Pat. No. 2,936,856 (May 17, 1960)

SUMMARY OF INVENTION

Technical Problem

The traditional lubricants however do not meet all of energy-saving, heat resistance, and low-temperature fluidity.

A lubricant having a lower viscosity is usually less heat-resistant. Therefore, as the speed at which a bearing which employs the traditional lubricants is rotated is increased for high-speed processing of large-volume information, the temperature inside the bearing increases due to the high-speed rotation of the bearing. As the temperature inside the bearing increases, the lubricant evaporates more. As a result, the bearing increases energy loss due to lack of lubrication inside the bearing. That is, in a case where a lubricant which is low in viscosity but is poor in heat-resistance is used as a bearing lubricant in pursuit of energy-saving, it is consequently not possible to achieve energy-saving of an electronic device.

In order to meet requirements such as high-speed processing of information and miniaturization of devices, a bearing lubricant is required to not only have the foregoing basic properties which lubricants should have but also be excellent in energy-saving and heat resistance as compared to traditional lubricants. That is, there is a demand for a lubricant which has a low viscosity and suffers less evaporation loss as compared to traditional lubricants. Moreover, in order that a lubricant is usable in a wide range of temperatures, the lubricant is required to be low in viscosity even at low temperature and to suffer less evaporation loss even at high temperature.

The present invention was made in view of the above problem, and an object of the present invention is to provide (i) a lubricant having not only the foregoing basic properties which the lubricant should have but also excellent energy-saving, heat-resistance and low-temperature fluidity as compared to traditional lubricants and (ii) use of the lubricant.

Solution to Problem

The inventors of the present invention made a diligent study in order to attain the object, and consequently obtained a novel compound having two or more ether bonds in a molecular structure of an alkyl chain of carboxylic acid which constitutes carboxylic acid monoester. The inventors of the present invention newly found that, by using the compound as a base oil of a lubricant, it was possible to reduce viscosity and improve heat resistance and low-temperature fluidity as compared to traditional lubricants. The inventors of the present invention completed the present invention on the basis of this new finding. Moreover, the inventors of the present invention found that a lubricant containing this compound is suitably usable as not only a bearing lubricant but also a freezer oil because this compound has a moderate compatibility with or solubility to a hydrocarbon coolant.

That is, a compound in accordance with the present invention is represented by the following general formula (1) and has a 40° C. kinetic viscosity (v) that satisfies 4 mm$^2$/s≤v≤30 mm$^2$/s,

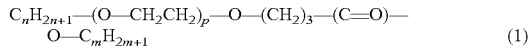
$$C_nH_{2n+1}-(O-CH_2CH_2)_p-O-(CH_2)_3-(C=O)-O-C_mH_{2m+1} \quad (1)$$

(where O represents an oxygen atom, C represents a carbon atom, H represents a hydrogen atom, m is an integer of 1 to 18, n is an integer of 1 to 12, p is an integer of 1 to 3, and 2≤n+m≤30 is satisfied).

The compound in accordance with the present invention is preferably such that in the general formula (1), m is an integer of 10 to 14, n is an integer of 1 to 12, p is 2, and 11≤n+m≤26 is satisfied, and the 40° C. kinetic viscosity (v) satisfies 4 mm2/s≤v≤20 mm2/s.

The compound in accordance with the present invention is preferably such that in the general formula (1), m is an integer of 1 to 14, n is an integer of 1 to 12, p is 1, and 5≤n+m≤26 is satisfied, and the 40° C. kinetic viscosity (v) satisfies 4 mm2/s≤v≤20 mm2/s.

The compound in accordance with the present invention is preferably such that in the general formula (1), m is an integer of 1 to 18, n is an integer of 1 to 12, p is 3, and 2≤n+m≤30 is satisfied.

The compound in accordance with the present invention is preferably such that m, n and p are 12, 8, and 2, respectively, in the general formula (1).

The compound in accordance with the present invention is preferably such that m, n and p are 14, 8, and 2, respectively, in the general formula (1).

The compound in accordance with the present invention is preferably such that m, n and p are 10, 8, and 2, respectively, in the general formula (1).

A lubricant in accordance with the present invention contains the compound in accordance with the present invention.

The lubricant in accordance with the present invention can be a lubricant for a fluid dynamic bearing or a lubricant for an impregnated bearing.

A bearing in accordance with the present invention is lubricated with use of the lubricant in accordance with the present invention.

The bearing in accordance with the present invention can be a fluid dynamic bearing or an impregnated bearing.

A method in accordance with the present invention of lubricating the bearing in accordance with the present invention includes the step of lubricating the bearing with use of the lubricant in accordance with the present invention.

A motor in accordance with the present invention includes the bearing in accordance with the present invention.

A method in accordance with the present invention of producing a grease in accordance with the present invention uses the lubricant in accordance with the present invention.

A grease in accordance with the present invention contains the lubricant in accordance with the present invention.

A freezer oil in accordance with the present invention contains the compound in accordance with the present invention.

Advantageous Effects of Invention

Since a lubricant in accordance with the present invention includes a compound of the present invention as a base oil, the lubricant is low in viscosity and excellent in heat resistance and low-temperature fluidity as compared to traditional lubricants. The heat resistance, the low-temperature fluidity, and energy-saving are well balanced.

It is therefore possible to achieve long-term stability and durability, etc. even in a case where a bearing is rotated at high speed, by using the lubricant in accordance with the present invention as a working fluid for lubricating the bearing. This allows the bearing to have a long life. The bearing can also improve energy-saving. It is further possible to provide a bearing usable in a wide range of temperatures.

On this account, the lubricant in accordance with the present invention is particularly excellent as a lubricant used for a bearing provided in a rotating device etc. of an electronic device (such as an audio-visual device, a server or a personal computer) which is required to decrease in size and weight and increase in memory capacity and information processing speed.

Since a freezer oil in accordance with the present invention contains the compound of the present invention as a base oil, the freezer oil is low in viscosity and excellent in heat resistance and low-temperature fluidity as compared to traditional freezer oils. Energy-saving, the heat resistance, and the low-temperature fluidity are well balanced. The compound of the present invention has a moderate compatibility with or solubility to a hydrocarbon coolant. The freezer oil in accordance with the present invention therefore shows a moderate compatibility with or solubility to a coolant in a wide range of temperatures from low temperature to high temperature, in a case where the freezer oil in accordance with the present invention is used as a freezer oil that employs a hydrocarbon coolant. This allows the freezer oil to remarkably improve its lubricity and thermal stability.

DESCRIPTION OF EMBODIMENTS

The following description will discuss an embodiment of the present invention in detail. The present invention, however, should not be limited to this. The present invention can be executed as an aspect which is variously modified within a described scope. All of academic documents and patent literatures which are described in this specification are cited as references in this specification. Unless otherwise specified in this specification, "A to B" indicative of a numerical range means "not less than A and not more than B".

(1) A compound in accordance with the present invention, (2) a lubricant in accordance with the present invention, (3) a bearing in accordance with the present invention, (4) a method in accordance with the present invention of lubricating a bearing, (5) a motor in accordance with the present invention, (6) a grease in accordance with the present invention, and (7) a freezer oil in accordance with the present invention will be described below in this order.

[1. Compound in Accordance with the Present Invention]

The compound in accordance with the present invention (hereinafter sometimes called "the compound of the present invention") is characterized in being represented by the following general formula (1) and having a 40° C. kinetic viscosity (v) that satisfies 4 mm$^2$/s≤v≤30 mm$^2$/s,

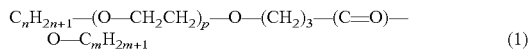

$$C_nH_{2n+1}\text{—}(O\text{—}CH_2CH_2)_p\text{—}O\text{—}(CH_2)_3\text{—}(C\text{=}O)\text{—}O\text{—}C_mH_{2m+1} \quad (1)$$

(where O represents an oxygen atom, C represents a carbon atom, H represents a hydrogen atom, m is an integer of 1 to 18, n is an integer of 1 to 12, p is an integer of 1 to 3, and 2≤n+m≤30 is satisfied).

In a case where the number of carbon atoms of the foregoing "CnH2n+1" in the general formula (1) is not more than 12, it is possible to secure low-temperature fluidity necessary for a lubricant.

A $C_1$-$C_{12}$ alkyl group of the foregoing "$C_nH_{2n+1}$" may have a straight-chain structure and a branched structure. Examples of the $C_1$-$C_{12}$ alkyl group include methyl group, ethyl group, propyl group, isopropyl group, butyl group, isobutyl group, amyl group, isoamyl group, hexyl group, cyclohexyl group, methylhexyl group, heptyl group, methylheptyl group, octyl group, 2-ethylhexyl group, nonyl group, isononyl group, 3,5,5-trimethylhexyl group, decyl group, isodecyl group, dodecyl group, and like groups.

In particular, the number of carbon atoms of the foregoing "$C_nH_{2n+1}$" is preferably 2 to 10, more preferably 4 to 8. In a case where the number of carbon atoms of the forgoing "$C_nH_{2n+1}$" is not more than 8, heat resistance and low-temperature fluidity which are necessary for a lubricant are well balanced. In a case where the number of carbon atoms of the foregoing "$C_nH_{2n+1}$" is not less than 4, an additive dissolves well.

In a case where the number of carbon atoms of the foregoing "$C_mH_{2m+1}$" in the general formula (1) is not more than 18, it is possible to secure low-temperature fluidity necessary for a lubricant.

A $C_1$-$C_8$ alkyl group of the foregoing "$C_mH_{2m+1}$" may have a straight-chain structure and a branched structure. Examples of the $C_1$-$C_{18}$ alkyl group include methyl group, ethyl group, propyl group, isopropyl group, butyl group, isobutyl group, amyl group, isoamyl group, hexyl group, cyclohexyl group, methylhexyl group, heptyl group, methylheptyl group, octyl group, 2-ethylhexyl group, nonyl group, isononyl group, 3,5,5-trimethylhexyl group, decyl group, isodecyl group, dodecyl group, tetradecyl group, hexadecyl group, octadecyl group, isooctadecyl group, and like groups.

In particular, in a case where p is 2, the number of carbon atoms of the foregoing "$C_mH_{2m+1}$" is preferably 4 to 14, more preferably 10 to 14. In a case where p is 2 and the number of carbon atoms of the foregoing "$C_mH_{2m+1}$" is not more than 14, it is possible to secure low-temperature fluidity necessary for a lubricant for a fluid dynamic bearing or a grease base oil. In a case where the number of carbon atoms of the foregoing "$C_mH_{2m+1}$" is not less than 10, it is possible to secure heat resistance suitable a lubricant for a fluid dynamic bearing or a grease base oil. In a case where p is 1, the number of carbon atoms of the foregoing "$C_mH_{2m+1}$" is preferably 1 to 18, more preferably 4 to 14. In a case where p is 1 and the number of carbon atoms of the foregoing "$C_mH_{2m+1}$" is not more than 14, it is possible to secure low-temperature fluidity necessary for a lubricant for a fluid dynamic bearing or a grease base oil. In a case where the number of carbon atoms of the foregoing "$C_mH_{2m+1}$" is not less than 4, it is possible to secure viscosity suitable for a lubricant.

The number of carbon atoms of the foregoing "$C_nH_{2n+1}$" and the number of carbon atoms of the foregoing "$C_mH_{2m+1}$" in the general formula (1) may be equal to or different from each other, provided that 2≤n+m≤30 is satisfied. It is preferable that 5≤n+m≤26 be satisfied. It is more preferable that 11≤n+m≤26 be satisfied. In a case where n+m is not less than 5, it is possible to secure viscosity suitable for a lubricant. In a case where n+m is not less than 11, it is possible to secure heat resistance suitable for a lubricant for a fluid dynamic bearing or a grease base oil. In a case where n+m is not more than 26, it is possible to obtain viscosity suitable for a lubricant for a fluid dynamic bearing or a grease base oil.

In a case where p is not less than 1 in the general formula (1), it is possible to obtain a low viscosity and a suitable low-temperature fluidity as compared to those of existing lubricants. In a case where p is not more than 3 in the general formula (1), it is possible to secure oiliness necessary for a lubricant. Note that a compound where p is not less than 4 increases water solubility, and therefore has difficulty being handled as a bearing lubricant or a grease base oil.

Examples of the compound represented by the general formula (1) include, in addition to compounds of Examples 1 through 18 (later described), 5,8-dioxanonanoic acid methyl ester, 5,8-dioxanonanoic acid ethyl ester, 5,8-dioxanonanoic acid propyl ester, 5,8-dioxanonanoic acid isopropyl ester, 5,8-dioxanonanoic acid butyl ester, 5,8-dioxanonanoic acid isobutyl ester, 5,8-dioxanonanoic acid amyl ester, 5,8-dioxanonanoic acid isoamyl ester, 5,8-dioxanonanoic acid hexyl ester, 5,8-dioxanonanoic acid cyclohexyl ester, 5,8-dioxanonanoic acid methylhexyl ester, 5,8-dioxanonanoic acid heptyl ester, 5,8-dioxanonanoic acid methylheptyl ester, 5,8-dioxanonanoic acid octyl ester, 5,8-dioxanonanoic acid 2-ethylhexyl ester, 5,8-dioxanonanoic acid nonyl ester, 5,8-dioxanonanoic acid isononyl ester, 5,8-dioxanonanoic acid 3,5,5-trimethylhexyl ester, 5,8-dioxanonanoic acid decyl ester, 5,8-dioxanonanoic acid isodecyl ester, 5,8-dioxanonanoic acid dodecyl ester, 5,8-dioxanonanoic acid tetradecyl ester, 5,8-dioxanonanoic acid hexadecyl ester, 5,8-dioxanonanoic acid 2-butyloctyl ester, 5,8-dioxanonanoic acid 2-hexyldecyl ester, 5,8-dioxanonanoic acid octadecyl ester, 5,8-dioxanonanoic acid isooctadecyl ester, 5,8-dioxadecanoic acid methyl ester, 5,8-dioxadecanoic acid ethyl ester, 5,8-dioxadecanoic acid propyl ester, 5,8-dioxadecanoic acid isopropyl ester, 5,8-dioxadecanoic acid butyl ester, 5,8-dioxadecanoic acid isobutyl ester, 5,8-dioxadecanoic acid amyl ester, 5,8-dioxadecanoic acid isoamyl ester, 5,8-dioxadecanoic acid hexyl ester, 5,8-dioxadecanoic acid cyclohexyl ester, 5,8-dioxadecanoic acid methylhexyl ester, 5,8-dioxadecanoic acid heptyl ester, 5,8-dioxadecanoic acid methylheptyl ester, 5,8-dioxadecanoic acid octyl ester, 5,8-dioxadecanoic acid 2-ethylhexyl ester, 5,8-dioxadecanoic acid nonyl ester, 5,8-dioxadecanoic acid isononyl ester, 5,8-dioxadecanoic acid 3,5,5-trimethylhexyl ester, 5,8-dioxadecanoic acid decyl ester, 5,8-dioxadecanoic acid isodecyl ester, 5,8-dioxadecanoic acid dodecyl ester, 5,8-dioxadecanoic acid tetradecyl ester, 5,8-dioxadecanoic acid hexadecyl ester, 5,8-dioxadecanoic acid 2-butyloctyl ester, 5,8-dioxadecanoic acid 2-hexyldecyl ester, 5,8-dioxadecanoic acid octadecyl ester, 5,8-dioxadecanoic acid isooctadecyl ester, 9-methyl-5,8-dioxadecanoic acid methyl ester, 9-methyl-5,8-dioxadecanoic acid ethyl ester, 9-methyl-5,8-dioxadecanoic acid propyl ester, 9-methyl-5,8-dioxadecanoic acid isopropyl ester, 9-methyl-5,8-dioxadecanoic acid butyl ester, 9-methyl-5,8-dioxadecanoic acid isobutyl ester, 9-methyl-5,8-dioxadecanoic acid amyl ester, 9-methyl-5,8-dioxadecanoic acid isoamyl ester, 9-methyl-5,8-dioxadecanoic acid hexyl ester, 9-methyl-5,8-dioxadecanoic acid cyclohexyl ester, 9-methyl-5,8-dioxaldecanoic acid methylhexyl ester, 9-methyl-5,8-dioxadecanoic acid heptyl ester, 9-methyl-5,8-dioxadecanoic acid methylheptyl ester, 9-methyl-5,8-dioxadecanoic acid octyl ester, 9-methyl-5,8-dioxadecanoic acid 2-ethylhexyl ester, 9-methyl-5,8-dioxadecanoic acid nonyl ester, 9-methyl-5,8-dioxadecanoic acid isononyl ester, 9-methyl-5,8-dioxadecanoic acid 3,5,5-trimethylhexyl ester, 9-methyl-5,8-dioxadecanoic acid decyl ester, 9-methyl-5,8-dioxadecanoic acid isodecyl ester, 9-methyl-5,8-dioxadecanoic acid dodecyl ester, 9-methyl-5,8-dioxadecanoic acid tetradecyl ester, 9-methyl-5,8-dioxadecanoic acid hexadecyl ester, 9-methyl-5,8-dioxadecanoic acid 2-butyloctyl ester, 9-methyl-5,8-dioxadecanoic acid 2-hexyldecyl ester, 9-methyl-5,8-dioxadecanoic acid octadecyl ester, 9-methyl-5,8-dioxadecanoic acid isooctadecyl ester, 5,8-dioxadodecanoic acid methyl ester, 5,8-dioxadodecanoic acid ethyl ester, 5,8-dioxadodecanoic acid propyl ester, 5,8-dioxadodecanoic acid isopropyl ester, 5,8-dioxadodecanoic acid butyl ester, 5,8-dioxadodecanoic acid isobutyl ester, 5,8-dioxadodecanoic acid amyl ester, 5,8-dioxadodecanoic acid isoamyl ester, 5,8-dioxadodecanoic acid hexyl ester, 5,8-dioxadodecanoic acid cyclohexyl ester, 5,8-dioxadodecanoic acid methylhexyl ester, 5,8-dioxadodecanoic acid heptyl ester, 5,8-dioxadodecanoic acid methylheptyl ester, 5,8-dioxadodecanoic acid octyl ester, 5,8-dioxadodecanoic acid 2-ethylhexyl ester, 5,8-dioxadodecanoic acid nonyl ester, 5,8-dioxadodecanoic acid isononyl ester, 5,8-dioxadodecanoic acid 3,5,5-trimethylhexyl ester, 5,8-dioxadodecanoic acid decyl ester, 5,8-dioxadodecanoic acid isodecyl ester, 5,8-dioxadodecanoic acid dodecyl ester, 5,8-dioxadodecanoic acid tetradecyl ester, 5,8-dioxadodecanoic acid hexadecyl ester, 5,8-dioxadodecanoic acid 2-butyloctyl ester, 5,8-dioxadodecanoic acid 2-hexyldecyl ester, 5,8-dioxadodecanoic acid octadecyl ester, 5,8-dioxadodecanoic acid isooctadecyl ester, 10-methyl-5,8-dioxaundecanoic acid methyl ester, 10-methyl-5,8-dioxaundecanoic acid ethyl ester, 10-methyl-5,8-dioxaundecanoic acid propyl ester, 10-methyl-5,8-dioxaundecanoic acid isopropyl ester, 10-methyl-5,8-dioxaundecanoic acid butyl ester, 10-methyl-5,8-dioxaundecanoic acid isobutyl ester, 10-methyl-5,8-dioxaundecanoic acid amyl ester, 10-methyl-5,8-dioxaundecanoic acid isoamyl ester, 10-methyl-5,8-dioxaundecanoic acid hexyl ester, 10-methyl-5,8-dioxaundecanoic acid cyclohexyl ester, 10-methyl-5,8-dioxaundecanoic acid methylhexyl ester, 10-methyl-5,8-dioxaundecanoic acid heptyl ester, 10-methyl-5,8-dioxaundecanoic acid methylheptyl ester, 10-methyl-5,8-dioxaundecanoic acid octyl ester, 10-methyl-5,8-dioxaundecanoic acid 2-ethylhexyl ester, 10-methyl-5,8-dioxaundecanoic acid nonyl ester, 10-methyl-5,8-dioxaundecanoic acid isononyl ester, 10-methyl-5,8-dioxaundecanoic acid 3,5,5-trimethylhexyl ester, 10-methyl-5,8-dioxaundecanoic acid decyl ester, 10-methyl-5,8-dioxaundecanoic acid isodecyl ester, 10-methyl-5,8-dioxaundecanoic acid dodecyl ester, 10-methyl-5,8-dioxaundecanoic acid tetradecyl ester, 10-methyl-5,8-dioxaundecanoic acid hexadecyl ester, 10-methyl-5,8-dioxaundecanoic acid 2-butyloctyl ester, 10-methyl-5,8-dioxaundecanoic acid 2-hexyldecyl ester, 10-methyl-5,8-dioxaundecanoic acid octadecyl ester, 10-methyl-5,8-dioxaundecanoic acid isooctadecyl ester, 5,8-dioxatridecanoic acid methyl ester, 5,8-dioxatridecanoic acid ethyl ester, 5,8-dioxatridecanoic acid propyl ester, 5,8-dioxatridecanoic acid isopropyl ester, 5,8-dioxatridecanoic acid butyl ester, 5,8-dioxatridecanoic acid isobutyl ester, 5,8-dioxatridecanoic acid amyl ester, 5,8-dioxatridecanoic acid isoamyl ester, 5,8-dioxatridecanoic acid hexyl ester, 5,8-dioxatridecanoic acid cyclohexyl ester, 5,8-dioxatridecanoic acid methylhexyl ester, 5,8-dioxatridecanoic acid heptyl ester, 5,8-dioxatridecanoic acid methylheptyl ester, 5,8-dioxatridecanoic acid octyl ester, 5,8-dioxatridecanoic acid 2-ethylhexyl ester, 5,8-dioxatridecanoic acid nonyl ester, 5,8-dioxatridecanoic acid isononyl ester, 5,8-dioxatridecanoic acid 3,5,5-trimethylhexyl ester, 5,8-dioxatridecanoic acid decyl ester, 5,8-dioxatridecanoic acid isodecyl ester, 5,8-dioxatridecanoic acid dodecyl ester, 5,8-dioxatridecanoic acid tetradecyl ester, 5,8-dioxatridecanoic acid hexadecyl ester, 5,8-dioxatridecanoic acid 2-butyloctyl ester, 5,8-dioxatridecanoic acid 2-hexyldecyl ester, 5,8-dioxatridecanoic acid octadecyl ester, 5,8-dioxatridecanoic acid isooctadecyl ester, 11-methyl-5,8-dioxadodecanoic acid methyl ester, 11-methyl-5,8-dioxadodecanoic acid ethyl ester, 11-methyl-5,8-dioxadodecanoic acid propyl ester, 11-methyl-5,8-dioxadodecanoic acid isopropyl ester, 11-methyl-5,8-dioxadodecanoic acid butyl ester, 11-methyl-5,8-dioxadodecanoic acid isobutyl ester, 11-methyl-5,8-dioxadodecanoic acid amyl ester, 11-methyl-5,8-dioxadodecanoic acid isoamyl ester, 11-methyl-5,8-dioxadodecanoic acid hexyl ester, 11-methyl-5,8-dioxadodecanoic acid cyclohexyl ester, 11-methyl-5,8-dioxadodecanoic acid methylhexyl ester, 11-methyl-5,8-dioxadodecanoic acid heptyl ester, 11-methyl-5,8-dioxadodecanoic acid methylheptyl ester, 11-methyl-5,8-dioxadodecanoic acid octyl ester, 11-methyl-5,8-dioxadodecanoic acid 2-ethylhexyl ester, 11-methyl-5,8-dioxadodecanoic acid nonyl ester, 11-methyl-5,8-dioxadodecanoic acid isononyl ester, 11-methyl-5,8-dioxadodecanoic acid 3,5,5-trimethylhexyl ester, 11-methyl-5,8-dioxadodecanoic acid decyl ester, 11-methyl-5,8-dioxadodecanoic acid isodecyl ester, 11-methyl-5,8-dioxadodecanoic acid dodecyl ester, 11-methyl-5,8-dioxadodecanoic acid tetradecyl ester, 11-methyl-5,8-dioxadodecanoic acid hexadecyl ester, 11-methyl-5,8-dioxadodecanoic acid 2-butyloctyl ester, 11-methyl-5,8-dioxadodecanoic acid 2-hexyldecyl ester, 11-methyl-5,8-dioxadodecanoic acid octadecyl ester, 11-methyl-5,8-dioxadodecanoic acid isooctadecyl ester, 5,8-dioxatetradecanoic acid methyl ester, 5,8-dioxatetradecanoic acid ethyl ester, 5,8-dioxatetradecanoic acid propyl ester, 5,8-dioxatetradecanoic acid isopropyl ester, 5,8-dioxatetradecanoic acid isobutyl ester, 5,8-dioxatetradecanoic acid amyl ester, 5,8-dioxatetradecanoic acid cyclohexyl ester, 5,8-dioxatetradecanoic acid methylhexyl ester, 5,8-dioxatetradecanoic acid heptyl ester, 5,8-dioxatetradecanoic acid methylheptyl ester, 5,8-dioxatetradecanoic acid octyl ester, 5,8-dioxatetradecanoic acid nonyl ester, 5,8-dioxatetradecanoic acid isononyl ester, 5,8-dioxatetradecanoic acid 3,5,5-trimethylhexyl ester, 5,8-dioxatetradecanoic acid decyl ester, 5,8-dioxatetradecanoic acid isodecyl ester, 5,8-dioxatetradecanoic acid tetradecyl ester, 5,8-dioxatetradecanoic acid hexadecyl ester, 5,8-dioxatetradecanoic acid 2-hexyldecyl ester, 5,8-dioxatetradecanoic acid octadecyl ester, 5,8-dioxatetradecanoic acid isooctadecyl ester, 5,8-dioxapentadecanoic acid methyl ester, 5,8-dioxapentadecanoic acid ethyl ester, 5,8-dioxapentadecanoic acid propyl ester, 5,8-dioxapentadecanoic acid isopropyl ester, 5,8-dioxapentadecanoic acid butyl ester, 5,8-dioxapentadecanoic acid isobutyl ester, 5,8-dioxapentadecanoic acid amyl ester, 5,8-dioxapentadecanoic acid isoamyl ester, 5,8-dioxapentadecanoic acid hexyl ester, 5,8-dioxapentadecanoic acid cyclohexyl ester, 5,8-dioxapentadecanoic acid methylhexyl ester, 5,8-dioxapentadecanoic acid heptyl ester, 5,8-dioxapentadecanoic acid methylheptyl ester, 5,8-dioxapentadecanoic acid octyl ester, 5,8-dioxapentadecanoic acid 2-ethylhexyl ester, 5,8-dioxapentadecanoic acid nonyl ester, 5,8-dioxapentadecanoic acid isononyl ester, 5,8-dioxapentadecanoic acid 3,5,5-trimethylhexyl ester, 5,8-dioxapentadecanoic acid decyl ester, 5,8-dioxapentadecanoic acid isodecyl ester, 5,8-dioxapentadecanoic acid dodecyl ester, 5,8-dioxapentadecanoic acid tetradecyl ester, 5,8-dioxapentadecanoic acid hexadecyl ester, 5,8-dioxapentadecanoic acid 2-butyloctyl ester, 5,8-dioxapentadecanoic acid 2-hexyldecyl ester, 5,8-dioxapentadecanoic acid octadecyl ester, 5,8-dioxapentadecanoic acid isooctadecyl ester, 10-ethyl-5,8-dioxatetradecanoic acid methyl ester, 10-ethyl-5,8-dioxatetradecanoic acid ethyl ester, 10-ethyl-5,8-dioxatetradecanoic acid propyl ester, 10-ethyl-5,8-dioxatetradecanoic acid isopropyl ester, 10-ethyl-5,8-dioxatetradecanoic acid butyl ester, 10-ethyl-5,8-dioxatetradecanoic acid isobutyl ester, 10-ethyl-5,8-dioxatetradecanoic acid amyl ester, 10-ethyl-5,8-dioxatetradecanoic acid isoamyl ester, 10-ethyl-5,8-dioxatetradecanoic acid hexyl ester, 10-ethyl-5,8-dioxatetradecanoic acid cyclohexyl ester, 10-ethyl-5,8-dioxatetradecanoic acid methylhexyl ester, 10-ethyl-5,8-dioxatetradecanoic acid heptyl ester, 10-ethyl-5,8-dioxatetradecanoic acid methylheptyl ester, 10-ethyl-5,8-dioxatetradecanoic acid 2-ethylhexyl ester, 10-ethyl-5,8-dioxatetradecanoic acid nonyl ester, 10-ethyl-5,8-dioxatetradecanoic acid isononyl ester, 10-ethyl-5,8-dioxatetradecanoic acid 3,5,5-trimethylhexyl ester, 10-ethyl-5,8-dioxatetradecanoic acid isodecyl ester, 10-ethyl-5,8-dioxatetradecanoic acid hexadecyl ester, 10-ethyl-5,8-dioxatetradecanoic acid 2-butyloctyl ester, 10-ethyl-5,8-dioxatetradecanoic acid 2-hexyldecyl ester, 10-ethyl-5,8-dioxatetradecanoic acid octadecyl ester, 10-ethyl-5,8-dioxatetradecanoic acid isooctadecyl ester, 5,8-dioxahexadecanoic acid methyl ester, 5,8-dioxahexadecanoic acid ethyl ester, 5,8-dioxahexadecanoic acid propyl ester, 5,8-dioxahexadecanoic acid isopropyl ester, 5,8-dioxahexadecanoic acid butyl ester, 5,8-dioxahexadecanoic acid isobutyl ester, 5,8-dioxahexadecanoic acid amyl ester, 5,8-dioxahexadecanoic acid isoamyl ester, 5,8-dioxahexadecanoic acid hexyl ester, 5,8-dioxahexadecanoic acid cyclohexyl ester, 5,8-dioxahexadecanoic acid methylhexyl ester, 5,8-dioxahexadecanoic acid heptyl ester, 5,8-dioxahexadecanoic acid methylheptyl ester, 5,8-dioxahexadecanoic acid octyl ester, 5,8-dioxahexadecanoic acid 2-ethylhexyl ester, 5,8-dioxahexadecanoic acid nonyl ester, 5,8-dioxahexadecanoic acid isononyl ester, 5,8-dioxahexadecanoic acid 3,5,5-trimethylhexyl ester, 5,8-dioxahexadecanoic acid decyl ester, 5,8-dioxahexadecanoic acid isodecyl ester, 5,8-dioxahexadecanoic acid dodecyl ester, 5,8-dioxahexadecanoic acid tetradecyl ester, 5,8-dioxahexadecanoic acid hexadecyl ester, 5,8-dioxahexadecanoic acid 2-butyloctyl ester, 5,8-dioxahexadecanoic acid 2-hexyldecyl ester, 5,8-dioxahexadecanoic acid octadecyl ester, 5,8-dioxahexadecanoic acid isooctadecyl ester, 5,8-dioxaheptadecanoic acid methyl ester, 5,8-dioxaheptadecanoic acid ethyl ester, 5,8-dioxaheptadecanoic acid propyl ester, 5,8-dioxaheptadecanoic acid isopropyl ester, 5,8-dioxaheptadecanoic acid butyl ester, 5,8-dioxaheptadecanoic acid isobutyl ester, 5,8-dioxaheptadecanoic acid amyl ester, 5,8-dioxaheptadecanoic acid isoamyl ester, 5,8-dioxaheptadecanoic acid hexyl ester, 5,8-dioxaheptadecanoic acid cyclohexyl ester, 5,8-dioxaheptadecanoic acid methylhexyl ester, 5,8-dioxaheptadecanoic acid heptyl ester, 5,8-dioxaheptadecanoic acid methylheptyl ester, 5,8-dioxaheptadecanoic acid octyl ester, 5,8-dioxaheptadecanoic acid 2-ethylhexyl ester, 5,8-dioxaheptadecanoic acid nonyl ester, 5,8-dioxaheptadecanoic acid isononyl ester, 5,8-dioxaheptadecanoic acid 3,5,5-trimethylhexyl ester, 5,8-dioxaheptadecanoic acid decyl ester, 5,8-dioxaheptadecanoic acid isodecyl ester, 5,8-dioxaheptadecanoic acid dodecyl ester, 5,8-dioxaheptadecanoic acid tetradecyl ester, 5,8-dioxaheptadecanoic acid hexadecyl ester, 5,8-dioxaheptadecanoic acid 2-butyloctyl ester, 5,8-dioxaheptadecanoic acid 2-hexyldecyl ester, 5,8-dioxaheptadecanoic acid octadecyl ester, 5,8-dioxaheptadecanoic acid isooctadecyl ester, 5,8-dioxaoctadecanoic acid methyl ester, 5,8-dioxaoctadecanoic acid ethyl ester, 5,8-dioxaoctadecanoic acid propyl ester, 5,8-dioxaoctadecanoic acid isopropyl ester, 5,8-dioxaoctadecanoic acid butyl ester, 5,8-dioxaoctadecanoic acid isobutyl ester, 5,8-dioxaoctadecanoic acid amyl ester, 5,8-dioxaoctadecanoic acid isoamyl ester, 5,8-dioxaoctadecanoic acid hexyl ester, 5,8-dioxaoctadecanoic acid cyclohexyl ester, 5,8-dioxaoctadecanoic acid methylhexyl ester, 5,8-dioxaoctadecanoic acid heptyl ester, 5,8-dioxaoctadecanoic acid methylheptyl ester, 5,8-dioxaoctadecanoic acid octyl ester, 5,8-dioxaoctadecanoic acid 2-ethylhexyl ester, 5,8-dioxaoctadecanoic acid nonyl ester, 5,8-dioxaoctadecanoic acid isononyl ester, 5,8-dioxaoctadecanoic acid 3,5,5-trimethylhexyl ester, 5,8-dioxaoctadecanoic acid decyl ester, 5,8-dioxaoctadecanoic acid isodecyl ester, 5,8-dioxaoctadecanoic acid dodecyl ester, 5,8-dioxaoctadecanoic acid tetradecyl ester, 5,8-dioxaoctadecanoic acid hexadecyl ester, 5,8-dioxaoctadecanoic acid 2-butyloctyl ester, 5,8-dioxaoctadecanoic acid 2-hexyldecyl ester, 5,8-dioxaoctadecanoic acid octadecyl ester, 5,8-dioxaoctadecanoic acid isooctadecyl ester, 5,8-dioxanonadecanoic acid methyl ester, 5,8-dioxanonadecanoic acid ethyl ester, 5,8-dioxanonadecanoic acid propyl ester, 5,8-dioxanonadecanoic acid isopropyl ester, 5,8-dioxanonadecanoic acid butyl ester, 5,8-dioxanonadecanoic acid isobutyl ester, 5,8-dioxanonadecanoic acid amyl ester, 5,8-dioxanonadecanoic acid isoamyl ester, 5,8-dioxanonadecanoic acid hexyl ester, 5,8-dioxanonadecanoic acid cyclohexyl ester, 5,8-dioxanonadecanoic acid methylhexyl ester, 5,8-dioxanonadecanoic acid heptyl ester, 5,8-dioxanonadecanoic acid methylheptyl ester, 5,8-dioxanonadecanoic acid octyl ester, 5,8-dioxanonadecanoic acid 2-ethylhexyl ester, 5,8-dioxanonadecanoic acid nonyl ester, 5,8-dioxanonadecanoic acid isononyl ester, 5,8-dioxanonadecanoic acid 3,5,5-trimethylhexyl ester, 5,8-dioxanonadecanoic acid decyl ester, 5,8-dioxanonadecanoic acid isodecyl ester, 5,8-dioxanonadecanoic acid dodecyl ester, 5,8-dioxanonadecanoic acid tetradecyl ester, 5,8-dioxanonadecanoic acid hexadecyl ester, 5,8-dioxanonadecanoic acid 2-butyloctyl ester, 5,8-dioxanonadecanoic acid 2-hexyldecyl ester, 5,8-dioxanonadecanoic acid octadecyl ester, 5,8-dioxanonadecanoic acid isooctadecyl ester, 5,8-dioxaicosanoic acid methyl ester, 5,8-dioxaicosanoic acid ethyl ester, 5,8-dioxaicosanoic acid propyl ester, 5,8-dioxaicosanoic acid isopropyl ester, 5,8-dioxaicosanoic acid butyl ester, 5,8-dioxaicosanoic acid isobutyl ester, 5,8-dioxaicosanoic acid amyl ester, 5,8-dioxaicosanoic acid isoamyl ester, 5,8-dioxaicosanoic acid hexyl ester, 5,8-dioxaicosanoic acid cyclohexyl ester, 5,8-dioxaicosanoic acid methylhexyl ester, 5,8-dioxaicosanoic acid heptyl ester, 5,8-dioxaicosanoic acid methylheptyl ester, 5,8-dioxaicosanoic acid octyl ester, 5,8-dioxaicosanoic acid 2-ethylhexyl ester, 5,8-dioxaicosanoic acid nonyl ester, 5,8-dioxaicosanoic acid isononyl ester, 5,8-dioxaicosanoic acid 3,5,5-trimethylhexyl ester, 5,8-dioxaicosanoic acid decyl ester, 5,8-dioxaicosanoic acid isodecyl ester, 5,8-dioxaicosanoic acid dodecyl ester, 5,8-dioxaicosanoic acid tetradecyl ester, 5,8-dioxaicosanoic acid hexadecyl ester, 5,8-dioxaicosanoic acid 2-butyloctyl ester, 5,8-dioxaicosanoic acid 2-hexyldecyl ester, 5,8-dioxaicosanoic acid octadecyl ester, 5,8-dioxaicosanoic acid isooctadecyl ester, 5,8,11-trioxadodecanoic acid methyl ester, 5,8,11-trioxadodecanoic acid ethyl ester, 5,8,11-trioxadodecanoic acid propyl ester, 5,8,11-trioxadodecanoic acid isopropyl ester, 5,8,11-trioxadodecanoic acid butyl ester, 5,8,11-trioxadodecanoic acid isobutyl ester, 5,8,11-trioxadodecanoic acid amyl ester, 5,8,11-trioxadodecanoic acid isoamyl ester, 5,8,11-trioxadodecanoic acid hexyl ester, 5,8,11-trioxadodecanoic acid cyclohexyl ester, 5,8,11-trioxadodecanoic acid methylhexyl ester, 5,8,11-trioxadodecanoic acid heptyl ester, 5,8,11-trioxadodecanoic acid methylheptyl ester, 5,8,11-trioxadodecanoic acid octyl ester, 5,8,11-trioxadodecanoic acid 2-ethylhexyl ester, 5,8,11-trioxadodecanoic acid nonyl ester, 5,8,11-trioxadodecanoic acid isononyl ester, 5,8,11-trioxadodecanoic acid 3,5,5-trimethylhexyl ester, 5,8,11-trioxadodecanoic acid decyl ester, 5,8,11-trioxadodecanoic acid isodecyl ester, 5,8,11-trioxadodecanoic acid dodecyl ester, 5,8,11-trioxadodecanoic acid tetradecyl ester, 5,8,11-trioxadodecanoic acid hexadecyl ester, 5,8,11-trioxadodecanoic acid octadecyl ester, 5,8,11-trioxadodecanoic acid isooctadecyl ester, 5,8,11-trioxatridecanoic acid ethyl ester, 5,8,11-trioxatridecanoic acid propyl ester, 5,8,11-trioxatridecanoic acid isopropyl ester, 5,8,11-trioxatridecanoic acid butyl ester, 5,8,11-trioxatridecanoic acid isobutyl ester, 5,8,11-trioxatridecanoic acid amyl ester, 5,8,11-trioxatridecanoic acid isoamyl ester, 5,8,11-trioxatridecanoic acid hexyl ester, 5,8,11-trioxatridecanoic acid cyclohexyl ester, 5,8,11-trioxatridecanoic acid methylhexyl ester, 5,8,11-trioxatridecanoic acid heptyl ester, 5,8,11-trioxatridecanoic acid methylheptyl ester, 5,8,11-trioxatridecanoic acid octyl ester, 5,8,11-trioxatridecanoic acid 2-ethylhexyl ester, 5,8,11-trioxatridecanoic acid nonyl ester, 5,8,11-trioxatridecanoic acid isononyl ester, 5,8,11-trioxatridecanoic acid 3,5,5-trimethylhexyl ester, 5,8,11-trioxatridecanoic acid decyl ester, 5,8,11-trioxatridecanoic acid isodecyl ester, 5,8,11-trioxatridecanoic acid dodecyl ester, 5,8,11-trioxatridecanoic acid tetradecyl ester, 5,8,11-trioxatridecanoic acid hexadecyl ester, 5,8,11-trioxatridecanoic acid 2-butyloctyl ester, 5,8,11-trioxatridecanoic acid 2-hexyldecyl ester, 5,8,11-trioxatridecanoic acid octadecyl ester, 5,8,11-trioxatridecanoic acid isooctadecyl ester, 12-methyl-5,8,11-trioxatridecanoic acid methyl ester, 12-methyl-5,8,11-trioxatridecanoic acid ethyl ester, 12-methyl-5,8,11-trioxatridecanoic acid propyl ester, 12-methyl-5,8,11-trioxatridecanoic acid isopropyl ester, 12-methyl-5,8,11-trioxatridecanoic acid butyl ester, 12-methyl-5,8,11-trioxatridecanoic acid isobutyl ester, 12-methyl-5,8,11-trioxatridecanoic acid amyl ester, 12-methyl-5,8,11-trioxatridecanoic acid isoamyl ester, 12-methyl-5,8,11-trioxatridecanoic acid hexyl ester, 12-methyl-5,8,11-trioxatridecanoic acid cyclohexyl ester, 12-methyl-5,8-dioxaldecanoic acid methylhexyl ester, 12-methyl-5,8,11-trioxatridecanoic acid heptyl ester, 12-methyl-5,8,11-trioxatridecanoic acid methylheptyl ester, 12-methyl-5,8,11-trioxatridecanoic acid octyl ester, 12-methyl-5,8,11-trioxatridecanoic acid 2-ethylhexyl ester, 12-methyl-5,8,11-trioxatridecanoic acid nonyl ester, 12-methyl-5,8,11-trioxatridecanoic acid isononyl ester, 12-methyl-5,8,11-trioxatridecanoic acid 3,5,5-trimethylhexyl ester, 12-methyl-5,8,11-trioxatridecanoic acid decyl ester, 12-methyl-5,8,11-trioxatridecanoic acid isodecyl ester, 12-methyl-5,8,11-trioxatridecanoic acid dodecyl ester, 12-methyl-5,8,11-trioxatridecanoic acid tetradecyl ester, 12-methyl-5,8,11-trioxatridecanoic acid hexadecyl ester, 12-methyl-5,8,11-trioxatridecanoic acid 2-butyloctyl ester, 12-methyl-5,8,11-trioxatridecanoic acid 2-hexyldecyl ester, 12-methyl-5,8,11-trioxatridecanoic acid octadecyl ester, 12-methyl-5,8,11-trioxatridecanoic acid isooctadecyl ester, 5,8,11-trioxapentadecanoic acid methyl ester, 5,8,11-trioxapentadecanoic acid ethyl ester, 5,8,11-trioxapentadecanoic acid propyl ester, 5,8,11-trioxapentadecanoic acid isopropyl ester, 5,8,11-trioxapentadecanoic acid butyl ester, 5,8,11-trioxapentadecanoic acid isobutyl ester, 5,8,11-trioxapentadecanoic acid amyl ester, 5,8,11-trioxapentadecanoic acid isoamyl ester, 5,8,11-trioxapentadecanoic acid hexyl ester, 5,8,11-trioxapentadecanoic acid cyclohexyl ester, 5,8,11-trioxapentadecanoic acid methylhexyl ester, 5,8,11-trioxapentadecanoic acid heptyl ester, 5,8,11-trioxapentadecanoic acid methylheptyl ester, 5,8,11-trioxapentadecanoic acid octyl ester, 5,8,11-trioxapentadecanoic acid 2-ethylhexyl ester, 5,8,11-trioxapentadecanoic acid nonyl ester, 5,8,11-trioxapentadecanoic acid isononyl ester, 5,8,11-trioxapentadecanoic acid 3,5,5-trimethylhexyl ester, 5,8,11-trioxapentadecanoic acid decyl ester, 5,8,11-trioxapentadecanoic acid isodecyl ester, 5,8,11-trioxapentadecanoic acid dodecyl ester, 5,8,11-trioxapentadecanoic acid tetradecyl ester, 5,8,11-trioxapentadecanoic acid hexadecyl ester, 5,8,11-trioxapentadecanoic acid 2-butyloctyl ester, 5,8,11-trioxapentadecanoic acid 2-hexyldecyl ester, 5,8,11-trioxapentadecanoic acid octadecyl ester, 5,8,11-trioxapentadecanoic acid isooctadecyl ester, 13-methyl-5,8,11-trioxatetradecanoic acid methyl ester, 13-methyl-5,8,11-trioxatetradecanoic acid ethyl ester, 13-methyl-5,8,11-trioxatetradecanoic acid propyl ester, 13-methyl-5,8,11-trioxatetradecanoic acid isopropyl ester, 13-methyl-5,8,11-trioxatetradecanoic acid butyl ester, 13-methyl-5,8,11-trioxatetradecanoic acid isobutyl ester, 13-methyl-5,8,11-trioxatetradecanoic acid amyl ester, 13-methyl-5,8,11-trioxatetradecanoic acid isoamyl ester, 13-methyl-5,8,11-trioxatetradecanoic acid hexyl ester, 10-methyl-5,8,11-trioxatetradecanoic acid cyclohexyl ester, 13-methyl-5,8,11-trioxatetradecanoic acid methylhexyl ester, 13-methyl-5,8,11-trioxatetradecanoic acid heptyl ester, 13-methyl-5,8,11-trioxatetradecanoic acid methylheptyl ester, 13-methyl-5,8,11-trioxatetradecanoic acid octyl ester, 13-methyl-5,8,11-trioxatetradecanoic acid 2-ethylhexyl ester, 13-methyl-5,8,11-trioxatetradecanoic acid nonyl ester, 13-methyl-5,8,11-trioxatetradecanoic acid isononyl ester, 13-methyl-5,8,11-trioxatetradecanoic acid 3,5,5-trimethylhexyl ester, 13-methyl-5,8,11-trioxatetradecanoic acid decyl ester, 13-methyl-5,8,11-trioxatetradecanoic acid isodecyl ester, 13-methyl-5,8,11-trioxatetradecanoic acid dodecyl ester, 13-methyl-5,8,11-trioxatetradecanoic acid tetradecyl ester, 13-methyl-5,8,11-trioxatetradecanoic acid hexadecyl ester, 13-methyl-5,8,11-trioxatetradecanoic acid 2-butyloctyl ester, 13-methyl-5,8,11-trioxatetradecanoic acid 2-hexyldecyl ester, 13-methyl-5,8,11-trioxatetradecanoic acid octadecyl ester, 13-methyl-5,8,11-trioxatetradecanoic acid isooctadecyl ester, 5,8,11-trioxahexadecanoic acid methyl ester, 5,8,11-trioxahexadecanoic acid ethyl ester, 5,8,11-trioxahexadecanoic acid propyl ester, 5,8,11-trioxahexadecanoic acid isopropyl ester, 5,8,11-trioxahexadecanoic acid butyl ester, 5,8,11-trioxahexadecanoic acid isobutyl ester, 5,8,11-trioxahexadecanoic acid amyl ester, 5,8,11-trioxahexadecanoic acid isoamyl ester, 5,8,11-trioxahexadecanoic acid hexyl ester, 5,8,11-trioxahexadecanoic acid cyclohexyl ester, 5,8,11-trioxahexadecanoic acid methylhexyl ester, 5,8,11-trioxahexadecanoic acid heptyl ester, 5,8,11-trioxahexadecanoic acid methylheptyl ester, 5,8,11-trioxahexadecanoic acid octyl ester, 5,8,11-trioxahexadecanoic acid 2-ethylhexyl ester, 5,8,11-trioxahexadecanoic acid nonyl ester, 5,8,11-trioxahexadecanoic acid isononyl ester, 5,8,11-trioxahexadecanoic acid 3,5,5-trimethylhexyl ester, 5,8,11-trioxahexadecanoic acid decyl ester, 5,8,11-trioxahexadecanoic acid isodecyl ester, 5,8,11-trioxahexadecanoic acid dodecyl ester, 5,8,11-trioxahexadecanoic acid tetradecyl ester, 5,8,11-trioxahexadecanoic acid hexadecyl ester, 5,8,11-trioxahexadecanoic acid 2-butyloctyl ester, 5,8,11-trioxahexadecanoic acid 2-hexyldecyl ester, 5,8,11-trioxahexadecanoic acid octadecyl ester, 5,8,11-trioxahexadecanoic acid isooctadecyl ester, 14-methyl-5,8,11-trioxapentadecanoic acid methyl ester, 14-methyl-5,8,11-trioxapentadecanoic acid ethyl ester, 14-methyl-5,8,11-trioxapentadecanoic acid propyl ester, 14-methyl-5,8,11-trioxapentadecanoic acid isopropyl ester, 14-methyl-5,8,11-trioxapentadecanoic acid butyl ester, 14-methyl-5,8,11-trioxapentadecanoic acid isobutyl ester, 14-methyl-5,8,11-trioxapentadecanoic acid amyl ester, 14-methyl-5,8,11-trioxapentadecanoic acid isoamyl ester, 14-methyl-5,8,11-trioxapentadecanoic acid hexyl ester, 14-methyl-5,8,11-trioxapentadecanoic acid cyclohexyl ester, 14-methyl-5,8,11-trioxapentadecanoic acid methylhexyl ester, 14-methyl-5,8,11-trioxapentadecanoic acid heptyl ester, 14-methyl-5,8,11-trioxapentadecanoic acid methylheptyl ester, 14-methyl-5,8,11-trioxapentadecanoic acid octyl ester, 14-methyl-5,8,11-trioxapentadecanoic acid 2-ethylhexyl ester, 14-methyl-5,8,11-trioxapentadecanoic acid nonyl ester, 14-methyl-5,8,11-trioxapentadecanoic acid isononyl ester, 14-methyl-5,8,11-trioxapentadecanoic acid 3,5,5-trimethylhexyl ester, 14-methyl-5,8,11-trioxapentadecanoic acid decyl ester, 14-methyl-5,8,11-trioxapentadecanoic acid isodecyl ester, 14-methyl-5,8,11-trioxapentadecanoic acid dodecyl ester, 14-methyl-5,8,11-trioxapentadecanoic acid tetradecyl ester, 14-methyl-5,8,11-trioxapentadecanoic acid hexadecyl ester, 14-methyl-5,8,11-trioxapentadecanoic acid 2-butyloctyl ester, 14-methyl-5,8,11-trioxapentadecanoic acid 2-hexyldecyl ester, 14-methyl-5,8,11-trioxapentadecanoic acid octadecyl ester, 14-methyl-5,8,11-trioxapentadecanoic acid isooctadecyl ester, 5,8,11-trioxaheptadecanoic acid methyl ester, 5,8,11-trioxaheptadecanoic acid ethyl ester, 5,8,11-trioxaheptadecanoic acid propyl ester, 5,8,11-trioxaheptadecanoic acid isopropyl ester, 5,8,11-trioxaheptadecanoic acid butyl ester, 5,8,11-trioxaheptadecanoic acid isobutyl ester, 5,8,11-trioxaheptadecanoic acid amyl ester, 5,8,11-trioxaheptadecanoic acid isoamyl ester, 5,8,11-trioxaheptadecanoic acid hexyl ester, 5,8,11-trioxaheptadecanoic acid cyclohexyl ester, 5,8,11-trioxaheptadecanoic acid methylhexyl ester, 5,8,11-trioxaheptadecanoic acid heptyl ester, 5,8,11-trioxaheptadecanoic acid methylheptyl ester, 5,8,11-trioxaheptadecanoic acid octyl ester, 5,8,11-trioxaheptadecanoic acid 2-ethylhexyl ester, 5,8,11-trioxaheptadecanoic acid nonyl ester, 5,8,11-trioxaheptadecanoic acid isononyl ester, 5,8,11-trioxaheptadecanoic acid 3,5,5-trimethylhexyl ester, 5,8,11-trioxaheptadecanoic acid decyl ester, 5,8,11-trioxaheptadecanoic acid isodecyl ester, 5,8,11-trioxaheptadecanoic acid tetradecyl ester, 5,8,11-trioxaheptadecanoic acid hexadecyl ester, 5,8,11-trioxaheptadecanoic acid 2-butyloctyl ester, 5,8,11-trioxaheptadecanoic acid 2-hexyldecyl ester, 5,8,11-trioxaheptadecanoic acid octadecyl ester, 5,8,11-trioxaheptadecanoic acid isooctadecyl ester, 5,8,11-trioxaoctadecanoic acid methyl ester, 5,8,11-trioxaoctadecanoic acid ethyl ester, 5,8,11-trioxaoctadecanoic acid propyl ester, 5,8,11-trioxaoctadecanoic acid isopropyl ester, 5,8,11-trioxaoctadecanoic acid butyl ester, 5,8,11-trioxaoctadecanoic acid isobutyl ester, 5,8,11-trioxaoctadecanoic acid amyl ester, 5,8,11-trioxaoctadecanoic acid isoamyl ester, 5,8,11-trioxaoctadecanoic acid hexyl ester, 5,8,11-trioxaoctadecanoic acid cyclohexyl ester, 5,8,11-trioxaoctadecanoic acid methylhexyl ester, 5,8,11-trioxaoctadecanoic acid heptyl ester, 5,8,11-trioxaoctadecanoic acid methylheptyl ester, 5,8,11-trioxaoctadecanoic acid octyl ester, 5,8,11-trioxaoctadecanoic acid 2-ethylhexyl ester, 5,8,11-trioxaoctadecanoic acid nonyl ester, 5,8,11-trioxaoctadecanoic acid isononyl ester, 5,8,11-trioxaoctadecanoic acid 3,5,5-trimethylhexyl ester, 5,8,11-trioxaoctadecanoic acid decyl ester, 5,8,11-trioxaoctadecanoic acid isodecyl ester, 5,8,11-trioxaoctadecanoic acid dodecyl ester, 5,8,11-trioxaoctadecanoic acid tetradecyl ester, 5,8,11-trioxaoctadecanoic acid hexadecyl ester, 5,8,11-trioxaoctadecanoic acid 2-butyloctyl ester, 5,8,11-trioxaoctadecanoic acid 2-hexyldecyl ester, 5,8,11-trioxaoctadecanoic acid octadecyl ester, 5,8,11-trioxaoctadecanoic acid isooctadecyl ester, 13-ethyl-5,8,11-trioxaheptadecanoic acid methyl ester, 13-ethyl-5,8,11-trioxaheptadecanoic acid ethyl ester, 13-ethyl-5,8,11-trioxaheptadecanoic acid propyl ester, 13-ethyl-5,8,11-trioxaheptadecanoic acid isopropyl ester, 13-ethyl-5,8,11-trioxaheptadecanoic acid butyl ester, 13-ethyl-5,8,11-trioxaheptadecanoic acid isobutyl ester, 13-ethyl-5,8,11-trioxaheptadecanoic acid amyl ester, 13-ethyl-5,8,11-trioxaheptadecanoic acid isoamyl ester, 13-ethyl-5,8,11-trioxaheptadecanoic acid hexyl ester, 13-ethyl-5,8,11-trioxaheptadecanoic acid cyclohexyl ester, 13-ethyl-5,8,11-trioxaheptadecanoic acid methylhexyl ester, 13-ethyl-5,8,11-trioxaheptadecanoic acid heptyl ester, 13-ethyl-5,8,11-trioxaheptadecanoic acid methylheptyl ester, 13-ethyl-5,8,11-trioxaheptadecanoic acid octyl ester, 13-ethyl-5,8,11-trioxaheptadecanoic acid 2-ethylhexyl ester, 13-ethyl-5,8, 11-trioxaheptadecanoic acid nonyl ester, 13-ethyl-5,8,11-trioxaheptadecanoic acid isononyl ester, 13-ethyl-5,8,11-trioxaheptadecanoic acid 3,5,5-trimethylhexyl ester, 13-ethyl-5,8,11-trioxaheptadecanoic acid isodecyl ester, 13-ethyl-5,8,11-trioxaheptadecanoic acid hexadecyl ester, 13-ethyl-5,8,11-trioxaheptadecanoic acid 2-butyloctyl ester, 13-ethyl-5,8,11-trioxaheptadecanoic acid 2-hexyldecyl ester, 13-ethyl-5,8,11-trioxaheptadecanoic acid octadecyl ester, 13-ethyl-5,8,11-trioxaheptadecanoic acid isooctadecyl ester, 5,8,11-trioxanonadecanoic acid methyl ester, 5,8,11-trioxanonadecanoic acid ethyl ester, 5,8,11-trioxanonadecanoic acid propyl ester, 5,8,11-trioxanonadecanoic acid isopropyl ester, 5,8,11-trioxanonadecanoic acid butyl ester, 5,8,11-trioxanonadecanoic acid isobutyl ester, 5,8,11-trioxanonadecanoic acid amyl ester, 5,8,11-trioxanonadecanoic acid isoamyl ester, 5,8,11-trioxanonadecanoic acid hexyl ester, 5,8,11-trioxanonadecanoic acid cyclohexyl ester, 5,8,11-trioxanonadecanoic acid methylhexyl ester, 5,8,11-trioxanonadecanoic acid heptyl ester, 5,8,11-trioxanonadecanoic acid methylheptyl ester, 5,8,11-trioxanonadecanoic acid octyl ester, 5,8,11-trioxanonadecanoic acid 2-ethylhexyl ester, 5,8,11-trioxanonadecanoic acid nonyl ester, 5,8,11-trioxanonadecanoic acid isononyl ester, 5,8,11-trioxanonadecanoic acid 3,5,5-trimethylhexyl ester, 5,8,11-trioxanonadecanoic acid decyl ester, 5,8,11-trioxanonadecanoic acid isodecyl ester, 5,8,11-trioxanonadecanoic acid dodecyl ester, 5,8,11-trioxanonadecanoic acid tetradecyl ester, 5,8,11-trioxanonadecanoic acid hexadecyl ester, 5,8,11-trioxanonadecanoic acid 2-butyloctyl ester, 5,8,11-trioxanonadecanoic acid 2-hexyldecyl ester, 5,8,11-trioxanonadecanoic acid octadecyl ester, 5,8,11-trioxanonadecanoic acid isooctadecyl ester, 5,8,11-trioxaicosanoic acid methyl ester, 5,8,11-trioxaicosanoic acid ethyl ester, 5,8,11-trioxaicosanoic acid propyl ester, 5,8,11-trioxaicosanoic acid isopropyl ester, 5,8,11-trioxaicosanoic acid butyl ester, 5,8,11-trioxaicosanoic acid isobutyl ester, 5,8,11-trioxaicosanoic acid amyl ester, 5,8,11-trioxaicosanoic acid isoamyl ester, 5,8,11-trioxaicosanoic acid hexyl ester, 5,8,11-trioxaicosanoic acid cyclohexyl ester, 5,8,11-trioxaicosanoic acid methylhexyl ester, 5,8,11-trioxaicosanoic acid heptyl ester, 5,8,11-trioxaicosanoic acid methylheptyl ester, 5,8,11-trioxaicosanoic acid octyl ester, 5,8,11-trioxaicosanoic acid 2-ethylhexyl ester, 5,8,11-trioxaicosanoic acid nonyl ester, 5,8,11-trioxaicosanoic acid isononyl ester, 5,8,11-trioxaicosanoic acid 3,5,5-trimethylhexyl ester, 5,8,11-trioxaicosanoic acid decyl ester, 5,8,11-trioxaicosanoic acid isodecyl ester, 5,8,11-trioxaicosanoic acid dodecyl ester, 5,8,11-trioxaicosanoic acid tetradecyl ester, 5,8,11-trioxaicosanoic acid hexadecyl ester, 5,8,11-trioxaicosanoic acid 2-butyloctyl ester, 5,8,11-trioxaicosanoic acid 2-hexyldecyl ester, 5,8,11-trioxaicosanoic acid octadecyl ester, 5,8,11-trioxaicosanoic acid isooctadecyl ester, 5,8,11-trioxahenicosanoic acid methyl ester, 5,8,11-trioxahenicosanoic acid ethyl ester, 5,8,11-trioxahenicosanoic acid propyl ester, 5,8,11-trioxahenicosanoic acid isopropyl ester, 5,8,11-trioxahenicosanoic acid butyl ester, 5,8,11-trioxahenicosanoic acid isobutyl ester, 5,8,11-trioxahenicosanoic acid amyl ester, 5,8,11-trioxahenicosanoic acid isoamyl ester, 5,8,11-trioxahenicosanoic acid hexyl ester, 5,8,11-trioxahenicosanoic acid cyclohexyl ester, 5,8,11-trioxahenicosanoic acid methylhexyl ester, 5,8,11-trioxahenicosanoic acid heptyl ester, 5,8,11-trioxahenicosanoic acid methylheptyl ester, 5,8,11-trioxahenicosanoic acid octyl ester, 5,8,11-trioxahenicosanoic acid 2-ethylhexyl ester, 5,8,11-trioxahenicosanoic acid nonyl ester, 5,8,11-trioxahenicosanoic acid isononyl ester, 5,8,11-trioxahenicosanoic acid 3,5,5-trimethylhexyl ester, 5,8,11-trioxahenicosanoic acid decyl ester, 5,8,11-trioxahenicosanoic acid isodecyl ester, 5,8,11-trioxahenicosanoic acid dodecyl ester, 5,8,11-trioxahenicosanoic acid tetradecyl ester, 5,8,11-trioxahenicosanoic acid hexadecyl ester, 5,8,11-trioxahenicosanoic acid 2-butyloctyl ester, 5,8,11-trioxahenicosanoic acid 2-hexyldecyl ester, 5,8,11-trioxahenicosanoic acid octadecyl ester, 5,8,11-trioxahenicosanoic acid isooctadecyl ester, 5,8,11-trioxadocosanoic acid methyl ester, 5,8,11-trioxadocosanoic acid ethyl ester, 5,8,11-trioxadocosanoic acid propyl ester, 5,8,11-trioxadocosanoic acid isopropyl ester, 5,8,11-trioxadocosanoic acid butyl ester, 5,8,11-trioxadocosanoic acid isobutyl ester, 5,8,11-trioxadocosanoic acid amyl ester, 5,8,11-trioxadocosanoic acid isoamyl ester, 5,8,11-trioxadocosanoic acid hexyl ester, 5,8,11-trioxadocosanoic acid cyclohexyl ester, 5,8,11-trioxadocosanoic acid methylhexyl ester, 5,8,11-trioxadocosanoic acid heptyl ester, 5,8,11-trioxadocosanoic acid methylheptyl ester, 5,8,11-trioxadocosanoic acid octyl ester, 5,8,11-trioxadocosanoic acid 2-ethylhexyl ester, 5,8,11-trioxadocosanoic acid nonyl ester, 5,8,11-trioxadocosanoic acid isononyl ester, 5,8,11-trioxadocosanoic acid 3,5,5-trimethylhexyl ester, 5,8,11-trioxadocosanoic acid decyl ester, 5,8,11-trioxadocosanoic acid isodecyl ester, 5,8,11-trioxadocosanoic acid dodecyl ester, 5,8,11-trioxadocosanoic acid tetradecyl ester, 5,8,11-trioxadocosanoic acid hexadecyl ester, 5,8,11-trioxadocosanoic acid 2-butyloctyl ester, 5,8,11-trioxadocosanoic acid 2-hexyldecyl ester, 5,8,11-trioxadocosanoic acid octadecyl ester, 5,8,11-trioxadocosanoic acid isooctadecyl ester, 5,8,11-trioxatricosanoic acid methyl ester, 5,8,11-trioxatricosanoic acid ethyl ester, 5,8,11-trioxatricosanoic acid propyl ester, 5,8,11-trioxatricosanoic acid isopropyl ester, 5,8,11-trioxatricosanoic acid butyl ester, 5,8,11-trioxatricosanoic acid isobutyl ester, 5,8,11-trioxatricosanoic acid amyl ester, 5,8,11-trioxatricosanoic acid isoamyl ester, 5,8,11-trioxatricosanoic acid hexyl ester, 5,8,11-trioxatricosanoic acid cyclohexyl ester, 5,8,11-trioxatricosanoic acid methylhexyl ester, 5,8,11-trioxatricosanoic acid heptyl ester, 5,8,11-trioxatricosanoic acid methylheptyl ester, 5,8,11-trioxatricosanoic acid octyl ester, 5,8,11-trioxatricosanoic acid 2-ethylhexyl ester, 5,8,11-trioxatricosanoic acid nonyl ester, 5,8,11-trioxatricosanoic acid isononyl ester, 5,8,11-trioxatricosanoic acid 3,5,5-trimethylhexyl ester, 5,8,11-trioxatricosanoic acid decyl ester, 5,8,11-trioxatricosanoic acid isodecyl ester, 5,8,11-trioxatricosanoic acid dodecyl ester, 5,8,11-trioxatricosanoic acid tetradecyl ester, 5,8,11-trioxatricosanoic acid hexadecyl ester, 5,8,11-trioxatricosanoic acid 2-butyloctyl ester, 5,8,11-trioxatricosanoic acid 2-hexyldecyl ester, 5,8,11-trioxatricosanoic acid octadecyl ester, 5,8,11-trioxatricosanoic acid isooctadecyl ester, 5,8,11,14-tetraoxapentadecanoic acid methyl ester, 5,8,11,14-tetraoxapentadecanoic acid ethyl ester, 5,8,11,14-tetraoxapentadecanoic acid propyl ester, 5,8,11,14-tetraoxapentadecanoic acid isopropyl ester, 5,8,11,14-tetraoxapentadecanoic acid butyl ester, 5,8,11,14-tetraoxapentadecanoic acid isobutyl ester, 5,8,11,14-tetraoxapentadecanoic acid amyl ester, 5,8,11,14-tetraoxapentadecanoic acid isoamyl ester, 5,8,11,14-tetraoxapentadecanoic acid hexyl ester, 5,8,11,14-tetraoxapentadecanoic acid cyclohexyl ester, 5,8,11,14-tetraoxapentadecanoic acid methylhexyl ester, 5,8,11,14-tetraoxapentadecanoic acid heptyl ester, 5,8,11,14-tetraoxapentadecanoic acid methylheptyl ester, 5,8,11,14-tetraoxapentadecanoic acid octyl ester, 5,8,11,14-tetraoxapentadecanoic acid 2-ethylhexyl ester, 5,8,11,14-tetraoxapentadecanoic acid nonyl ester, 5,8,11,14-tetraoxapentadecanoic acid isononyl ester, 5,8,11,14-tetraoxapentadecanoic acid 3,5,5-trimethylhexyl ester, 5,8,11,14-tetraoxapentadecanoic acid decyl ester, 5,8,11,14-tetraoxapentadecanoic acid isodecyl ester, 5,8,11,14- tetraoxapentadecanoic acid dodecyl ester, 5,8,11,14-tetraoxapentadecanoic acid tetradecyl ester, 5,8,11,14-tetraoxapentadecanoic acid hexadecyl ester, 5,8,11,14-tetraoxapentadecanoic acid 2-butyloctyl ester, 5,8,11,14-tetraoxapentadecanoic acid 2-hexyldecyl ester, 5,8,11,14-tetraoxapentadecanoic acid octadecyl ester, 5,8,11,14-tetraoxapentadecanoic acid isooctadecyl ester, 5,8,11,14-tetraoxahexadecanoic acid methyl ester, 5,8,11,14-tetraoxahexadecanoic acid ethyl ester, 5,8,11,14-tetraoxahexadecanoic acid propyl ester, 5,8,11,14-tetraoxahexadecanoic acid isopropyl ester, 5,8,11,14-tetraoxahexadecanoic acid butyl ester, 5,8,11,14-tetraoxahexadecanoic acid isobutyl ester, 5,8,11,14-tetraoxahexadecanoic acid amyl ester, 5,8,11,14-tetraoxahexadecanoic acid isoamyl ester, 5,8,11,14-tetraoxahexadecanoic acid hexyl ester, 5,8,11,14-tetraoxahexadecanoic acid cyclohexyl ester, 5,8,11,14-tetraoxahexadecanoic acid methylhexyl ester, 5,8,11,14-tetraoxahexadecanoic acid heptyl ester, 5,8,11,14-tetraoxahexadecanoic acid methylheptyl ester, 5,8,11,14-tetraoxahexadecanoic acid octyl ester, 5,8,11,14-tetraoxahexadecanoic acid 2-ethylhexyl ester, 5,8,11,14-tetraoxahexadecanoic acid nonyl ester, 5,8,11,14-tetraoxahexadecanoic acid isononyl ester, 5,8,11,14-tetraoxahexadecanoic acid 3,5,5-trimethylhexyl ester, 5,8,11,14-tetraoxahexadecanoic acid decyl ester, 5,8,11,14-tetraoxahexadecanoic acid isodecyl ester, 5,8,11,14-tetraoxahexadecanoic acid dodecyl ester, 5,8,11,14-tetraoxahexadecanoic acid tetradecyl ester, 5,8,11,14-tetraoxahexadecanoic acid hexadecyl ester, 5,8,11,14-tetraoxahexadecanoic acid 2-butyloctyl ester, 5,8,11,14-tetraoxahexadecanoic acid 2-hexyldecyl ester, 5,8,11,14-tetraoxahexadecanoic acid octadecyl ester, 5,8,11,14-tetraoxahexadecanoic acid isooctadecyl ester, 9-methyl-5,8,11,14-tetraoxahexadecanoic acid methyl ester, 9-methyl-5,8,11,14-tetraoxahexadecanoic acid ethyl ester, 9-methyl-5,8,11,14-tetraoxahexadecanoic acid propyl ester, 9-methyl-5,8,11,14-tetraoxahexadecanoic acid isopropyl ester, 9-methyl-5,8,11,14-tetraoxahexadecanoic acid butyl ester, 9-methyl-5,8,11,14-tetraoxahexadecanoic acid isobutyl ester, 9-methyl-5,8,11,14-tetraoxahexadecanoic acid amyl ester, 9-methyl-5,8,11,14-tetraoxahexadecanoic acid isoamyl ester, 9-methyl-5,8,11,14-tetraoxahexadecanoic acid hexyl ester, 9-methyl-5,8,11,14-tetraoxahexadecanoic acid cyclohexyl ester, 9-methyl-5,8-dioxaldecanoic acid methylhexyl ester, 9-methyl-5,8,11,14-tetraoxahexadecanoic acid heptyl ester, 9-methyl-5,8,11,14-tetraoxahexadecanoic acid methylheptyl ester, 9-methyl-5,8,11,14-tetraoxahexadecanoic acid octyl ester, 9-methyl-5,8,11,14-tetraoxahexadecanoic acid 2-ethylhexyl ester, 9-methyl-5,8,11,14-tetraoxahexadecanoic acid nonyl ester, 9-methyl-5,8,11,14-tetraoxahexadecanoic acid isononyl ester, 9-methyl-5,8,11,14-tetraoxahexadecanoic acid 3,5,5-trimethylhexyl ester, 9-methyl-5,8,11,14-tetraoxahexadecanoic acid decyl ester, 9-methyl-5,8,11,14-tetraoxahexadecanoic acid isodecyl ester, 9-methyl-5,8,11,14-tetraoxahexadecanoic acid dodecyl ester, 9-methyl-5,8,11,14-tetraoxahexadecanoic acid tetradecyl ester, 9-methyl-5,8,11,14-tetraoxahexadecanoic acid hexadecyl ester, 9-methyl-5,8,11,14-tetraoxahexadecanoic acid 2-butyloctyl ester, 9-methyl-5,8,11,14-tetraoxahexadecanoic acid 2-hexyldecyl ester, 9-methyl-5,8,11,14-tetraoxahexadecanoic acid octadecyl ester, 9-methyl-5,8,11,14-tetraoxahexadecanoic acid isooctadecyl ester, 5,8,11,14-tetraoxaoctadecanoic acid methyl ester, 5,8,11,14-tetraoxaoctadecanoic acid ethyl ester, 5,8,11,14-tetraoxaoctadecanoic acid propyl ester, 5,8,11,14-tetraoxaoctadecanoic acid isopropyl ester, 5,8,11,14-tetraoxaoctadecanoic acid butyl ester, 5,8,11,14-tetraoxaoctadecanoic acid isobutyl ester, 5,8,11,14-tetraoxaoctadecanoic acid amyl ester, 5,8,11,14-tetraoxaoctadecanoic acid isoamyl ester, 5,8,11,14-tetraoxaoctadecanoic acid hexyl ester, 5,8,11,14-tetraoxaoctadecanoic acid cyclohexyl ester, 5,8,11,14-tetraoxaoctadecanoic acid methylhexyl ester, 5,8,11,14-tetraoxaoctadecanoic acid heptyl ester, 5,8,11,14-tetraoxaoctadecanoic acid methylheptyl ester, 5,8,11,14-tetraoxaoctadecanoic acid octyl ester, 5,8,11,14-tetraoxaoctadecanoic acid nonyl ester, 5,8,11,14-tetraoxaoctadecanoic acid isononyl ester, 5,8,11,14-tetraoxaoctadecanoic acid 3,5,5-trimethylhexyl ester, 5,8,11,14-tetraoxaoctadecanoic acid decyl ester, 5,8,11,14-tetraoxaoctadecanoic acid isodecyl ester, 5,8,11,14-tetraoxaoctadecanoic acid dodecyl ester, 5,8,11,14-tetraoxaoctadecanoic acid tetradecyl ester, 5,8,11,14-tetraoxaoctadecanoic acid hexadecyl ester, 5,8,11,14-tetraoxaoctadecanoic acid 2-hexyldecyl ester, 5,8,11,14-tetraoxaoctadecanoic acid octadecyl ester, 5,8,11,14-tetraoxaoctadecanoic acid isooctadecyl ester, 16-methyl-5,8,11,14-tetraoxaheptadecanoic acid methyl ester, 16-methyl-5,8,11,14-tetraoxaheptadecanoic acid ethyl ester, 16-methyl-5,8,11,14-tetraoxaheptadecanoic acid propyl ester, 16-methyl-5,8,11,14-tetraoxaheptadecanoic acid isopropyl ester, 16-methyl-5,8,11,14-tetraoxaheptadecanoic acid butyl ester, 16-methyl-5,8,11,14-tetraoxaheptadecanoic acid isobutyl ester, 16-methyl-5,8,11,14-tetraoxaheptadecanoic acid amyl ester, 16-methyl-5,8,11,14-tetraoxaheptadecanoic acid isoamyl ester, 16-methyl-5,8,11,14-tetraoxaheptadecanoic acid hexyl ester, 16-methyl-5,8,11,14-tetraoxaheptadecanoic acid cyclohexyl ester, 16-methyl-5,8,11,14-tetraoxaheptadecanoic acid methylhexyl ester, 16-methyl-5,8,11,14-tetraoxaheptadecanoic acid heptyl ester, 16-methyl-5,8,11,14-tetraoxaheptadecanoic acid methylheptyl ester, 16-methyl-5,8,11,14-tetraoxaheptadecanoic acid octyl ester, 16-methyl-5,8,11,14-tetraoxaheptadecanoic acid 2-ethylhexyl ester, 16-methyl-5,8,11,14-tetraoxaheptadecanoic acid nonyl ester, 16-methyl-5,8,11,14-tetraoxaheptadecanoic acid isononyl ester, 16-methyl-5,8,11,14-tetraoxaheptadecanoic acid 3,5,5-trimethylhexyl ester, 16-methyl-5,8,11,14-tetraoxaheptadecanoic acid decyl ester, 16-methyl-5,8,11,14-tetraoxaheptadecanoic acid isodecyl ester, 16-methyl-5,8,11,14-tetraoxaheptadecanoic acid dodecyl ester, 16-methyl-5,8,11,14-tetraoxaheptadecanoic acid tetradecyl ester, 16-methyl-5,8,11,14-tetraoxaheptadecanoic acid hexadecyl ester, 16-methyl-5,8,11,14-tetraoxaheptadecanoic acid 2-butyloctyl ester, 16-methyl-5,8,11,14-tetraoxaheptadecanoic acid 2-hexyldecyl ester, 16-methyl-5,8,11,14-tetraoxaheptadecanoic acid octadecyl ester, 16-methyl-5,8,11,14-tetraoxaheptadecanoic acid isooctadecyl ester, 5,8,11,14-tetraoxanonadecanoic acid methyl ester, 5,8,11,14-tetraoxanonadecanoic acid ethyl ester, 5,8,11,14-tetraoxanonadecanoic acid propyl ester, 5,8,11,14-tetraoxanonadecanoic acid isopropyl ester, 5,8,11,14-tetraoxanonadecanoic acid butyl ester, 5,8,11,14-tetraoxanonadecanoic acid isobutyl ester, 5,8,11,14-tetraoxanonadecanoic acid amyl ester, 5,8,11,14-tetraoxanonadecanoic acid isoamyl ester, 5,8,11,14-tetraoxanonadecanoic acid hexyl ester, 5,8,11,14-tetraoxanonadecanoic acid cyclohexyl ester, 5,8,11,14-tetraoxanonadecanoic acid methylhexyl ester, 5,8,11,14-tetraoxanonadecanoic acid heptyl ester, 5,8,11,14-tetraoxanonadecanoic acid methylheptyl ester, 5,8,11,14-tetraoxanonadecanoic acid octyl ester, 5,8,11,14-tetraoxanonadecanoic acid 2-ethylhexyl ester, 5,8,11,14-tetraoxanonadecanoic acid nonyl ester, 5,8,11,14-tetraoxanonadecanoic acid isononyl ester, 5,8,11,14-tetraoxanonadecanoic acid 3,5,5-trimethylhexyl ester, 5,8, 11,14-tetraoxanonadecanoic acid decyl ester, 5,8,11,14-tetraoxanonadecanoic acid isodecyl ester, 5,8,11,14-tetraoxanonadecanoic acid dodecyl ester, 5,8,11,14-tetraoxanonadecanoic acid tetradecyl ester, 5,8,11,14-tetraoxanonadecanoic acid hexadecyl ester, 5,8,11,14-tetraoxanonadecanoic acid 2-butyloctyl ester, 5,8,11,14-tetraoxanonadecanoic acid 2-hexyldecyl ester, 5,8,11,14-tetraoxanonadecanoic acid octadecyl ester, 5,8,11,14-tetraoxanonadecanoic acid isooctadecyl ester, 17-methyl-5,8,11,14-tetraoxaoctadecanoic acid methyl ester, 17-methyl-5,8,11,14-tetraoxaoctadecanoic acid ethyl ester, 17-methyl-5,8,11,14-tetraoxaoctadecanoic acid propyl ester, 17-methyl-5,8,11,14-tetraoxaoctadecanoic acid isopropyl ester, 17-methyl-5,8,11,14-tetraoxaoctadecanoic acid butyl ester, 17-methyl-5,8,11,14-tetraoxaoctadecanoic acid isobutyl ester, 17-methyl-5,8,11,14-tetraoxaoctadecanoic acid amyl ester, 17-methyl-5,8,11,14-tetraoxaoctadecanoic acid isoamyl ester, 17-methyl-5,8,11,14-tetraoxaoctadecanoic acid hexyl ester, 17-methyl-5,8,11,14-tetraoxaoctadecanoic acid cyclohexyl ester, 17-methyl-5,8,11,14-tetraoxaoctadecanoic acid methylhexyl ester, 17-methyl-5,8,11,14-tetraoxaoctadecanoic acid heptyl ester, 17-methyl-5,8,11,14-tetraoxaoctadecanoic acid methylheptyl ester, 17-methyl-5,8,11,14-tetraoxaoctadecanoic acid octyl ester, 17-methyl-5,8,11,14-tetraoxaoctadecanoic acid 2-ethylhexyl ester, 17-methyl-5,8,11,14-tetraoxaoctadecanoic acid nonyl ester, 17-methyl-5,8,11,14-tetraoxaoctadecanoic acid isononyl ester, 17-methyl-5,8,11,14-tetraoxaoctadecanoic acid 3,5,5-trimethylhexyl ester, 17-methyl-5,8,11,14-tetraoxaoctadecanoic acid decyl ester, 17-methyl-5,8,11,14-tetraoxaoctadecanoic acid isodecyl ester, 17-methyl-5,8,11,14-tetraoxaoctadecanoic acid dodecyl ester, 17-methyl-5,8,11,14-tetraoxaoctadecanoic acid tetradecyl ester, 17-methyl-5,8,11,14-tetraoxaoctadecanoic acid hexadecyl ester, 17-methyl-5,8,11,14-tetraoxaoctadecanoic acid 2-butyloctyl ester, 17-methyl-5,8,11,14-tetraoxaoctadecanoic acid 2-hexyldecyl ester, 17-methyl-5,8,11,14-tetraoxaoctadecanoic acid octadecyl ester, 17-methyl-5,8,11,14-tetraoxaoctadecanoic acid isooctadecyl ester, 5,8,11,14-tetraoxaicosanoic acid methyl ester, 5,8,11,14-tetraoxaicosanoic acid ethyl ester, 5,8,11,14-tetraoxaicosanoic acid propyl ester, 5,8,11,14-tetraoxaicosanoic acid isopropyl ester, 5,8,11,14-tetraoxaicosanoic acid butyl ester, 5,8,11,14-tetraoxaicosanoic acid isobutyl ester, 5,8,11,14-tetraoxaicosanoic acid amyl ester, 5,8,11,14-tetraoxaicosanoic acid isoamyl ester, 5,8,11,14-tetraoxaicosanoic acid hexyl ester, 5,8,11,14-tetraoxaicosanoic acid cyclohexyl ester, 5,8,11,14-tetraoxaicosanoic acid methylhexyl ester, 5,8,11,14-tetraoxaicosanoic acid heptyl ester, 5,8,11,14-tetraoxaicosanoic acid methylheptyl ester, 5,8,11,14-tetraoxaicosanoic acid octyl ester, 5,8,11,14-tetraoxaicosanoic acid 2-ethylhexyl ester, 5,8,11,14-tetraoxaicosanoic acid nonyl ester, 5,8,11,14-tetraoxaicosanoic acid isononyl ester, 5,8,11,14-tetraoxaicosanoic acid 3,5,5-trimethylhexyl ester, 5,8,11,14-tetraoxaicosanoic acid decyl ester, 5,8,11,14-tetraoxaicosanoic acid isodecyl ester, 5,8,11,14-tetraoxaicosanoic acid dodecyl ester, 5,8,11,14-tetraoxaicosanoic acid tetradecyl ester, 5,8,11,14-tetraoxaicosanoic acid hexadecyl ester, 5,8,11,14-tetraoxaicosanoic acid 2-butyloctyl ester, 5,8,11,14-tetraoxaicosanoic acid 2-hexyldecyl ester, 5,8,11,14-tetraoxaicosanoic acid octadecyl ester, 5,8,11,14-tetraoxaicosanoic acid isooctadecyl ester, 5,8,11,14-tetraoxahenicosanoic acid methyl ester, 5,8,11,14-tetraoxahenicosanoic acid ethyl ester, 5,8,11,14-tetraoxahenicosanoic acid propyl ester, 5,8,11,14-tetraoxahenicosanoic acid isopropyl ester, 5,8,11,14-tetraoxahenicosanoic acid butyl ester, 5,8,11,14-tetraoxahenicosanoic acid isobutyl ester, 5,8,11,14-tetraoxahenicosanoic acid amyl ester, 5,8,11,14-tetraoxahenicosanoic acid isoamyl ester, 5,8,11,14-tetraoxahenicosanoic acid hexyl ester, 5,8,11,14-tetraoxahenicosanoic acid cyclohexyl ester, 5,8,11,14-tetraoxahenicosanoic acid methylhexyl ester, 5,8,11,14-tetraoxahenicosanoic acid heptyl ester, 5,8,11,14-tetraoxahenicosanoic acid methylheptyl ester, 5,8,11,14-tetraoxahenicosanoic acid octyl ester, 5,8,11,14-tetraoxahenicosanoic acid 2-ethylhexyl ester, 5,8,11,14-tetraoxahenicosanoic acid nonyl ester, 5,8,11,14-tetraoxahenicosanoic acid isononyl ester, 5,8,11,14-tetraoxahenicosanoic acid 3,5,5-trimethylhexyl ester, 5,8,11,14-tetraoxahenicosanoic acid decyl ester, 5,8,11,14-tetraoxahenicosanoic acid isodecyl ester, 5,8,11,14-tetraoxahenicosanoic acid dodecyl ester, 5,8,11,14-tetraoxahenicosanoic acid tetradecyl ester, 5,8,11,14-tetraoxahenicosanoic acid hexadecyl ester, 5,8,11,14-tetraoxahenicosanoic acid 2-butyloctyl ester, 5,8,11,14-tetraoxahenicosanoic acid 2-hexyldecyl ester, 5,8,11,14-tetraoxahenicosanoic acid octadecyl ester, 5,8,11,14-tetraoxahenicosanoic acid isooctadecyl ester, 16-ethyl-5,8,11,14-tetraoxaicosanoic acid methyl ester, 16-ethyl-5,8,11,14-tetraoxaicosanoic acid ethyl ester, 16-ethyl-5,8,11,14-tetraoxaicosanoic acid propyl ester, 16-ethyl-5,8,11,14-tetraoxaicosanoic acid isopropyl ester, 16-ethyl-5,8,11,14-tetraoxaicosanoic acid butyl ester, 16-ethyl-5,8,11,14-tetraoxaicosanoic acid isobutyl ester, 16-ethyl-5,8,11,14-tetraoxaicosanoic acid amyl ester, 16-ethyl-5,8,11,14-tetraoxaicosanoic acid isoamyl ester, 16-ethyl-5,8,11,14-tetraoxaicosanoic acid hexyl ester, 16-ethyl-5,8,11,14-tetraoxaicosanoic acid cyclohexyl ester, 16-ethyl-5,8,11,14-tetraoxaicosanoic acid methylhexyl ester, 16-ethyl-5,8,11,14-tetraoxaicosanoic acid heptyl ester, 16-ethyl-5,8,11,14-tetraoxaicosanoic acid methylheptyl ester, 16-ethyl-5,8,11,14-tetraoxaicosanoic acid octyl ester, 16-ethyl-5,8,11,14-tetraoxaicosanoic acid 2-ethylhexyl ester, 16-ethyl-5,8,11,14-tetraoxaicosanoic acid nonyl ester, 16-ethyl-5,8,11,14-tetraoxaicosanoic acid isononyl ester, 16-ethyl-5,8,11,14-tetraoxaicosanoic acid 3,5,5-trimethylhexyl ester, 16-ethyl-5,8,11,14-tetraoxaicosanoic acid decyl ester, 16-ethyl-5,8,11,14-tetraoxaicosanoic acid isodecyl ester, 16-ethyl-5,8,11,14-tetraoxaicosanoic acid dodecyl ester, 16-ethyl-5,8,11,14-tetraoxaicosanoic acid tetradecyl ester, 16-ethyl-5,8,11,14-tetraoxaicosanoic acid hexadecyl ester, 16-ethyl-5,8,11,14-tetraoxaicosanoic acid 2-butyloctyl ester, 16-ethyl-5,8,11,14-tetraoxaicosanoic acid 2-hexyldecyl ester, 16-ethyl-5,8,11,14-tetraoxaicosanoic acid octadecyl ester, 16-ethyl-5,8,11,14-tetraoxaicosanoic acid isooctadecyl ester, 5,8,11,14-tetraoxadocosanoic acid methyl ester, 5,8,11,14-tetraoxadocosanoic acid ethyl ester, 5,8,11,14-tetraoxadocosanoic acid propyl ester, 5,8,11,14-tetraoxadocosanoic acid isopropyl ester, 5,8,11,14-tetraoxadocosanoic acid butyl ester, 5,8,11,14-tetraoxadocosanoic acid isobutyl ester, 5,8,11,14-tetraoxadocosanoic acid amyl ester, 5,8,11,14-tetraoxadocosanoic acid isoamyl ester, 5,8,11,14-tetraoxadocosanoic acid hexyl ester, 5,8,11,14-tetraoxadocosanoic acid cyclohexyl ester, 5,8,11,14-tetraoxadocosanoic acid methylhexyl ester, 5,8,11,14-tetraoxadocosanoic acid heptyl ester, 5,8,11,14-tetraoxadocosanoic acid methylheptyl ester, 5,8,11,14-tetraoxadocosanoic acid octyl ester, 5,8,11,14-tetraoxadocosanoic acid 2-ethylhexyl ester, 5,8,11,14-tetraoxadocosanoic acid nonyl ester, 5,8,11,14-tetraoxadocosanoic acid isononyl ester, 5,8,11,14-tetraoxadocosanoic acid 3,5,5-trimethylhexyl ester, 5,8,11,14-tetraoxadocosanoic acid decyl ester, 5,8,11,14- tetraoxadocosanoic acid isodecyl ester, 5,8,11,14-tetraoxadocosanoic acid dodecyl ester, 5,8,11,14-tetraoxadocosanoic acid tetradecyl ester, 5,8,11,14-tetraoxadocosanoic acid hexadecyl ester, 5,8,11,14-tetraoxadocosanoic acid 2-butyloctyl ester, 5,8,11,14-tetraoxadocosanoic acid 2-hexyldecyl ester, 5,8,11,14-tetraoxadocosanoic acid octadecyl ester, 5,8,11,14-tetraoxadocosanoic acid isooctadecyl ester, 5,8,11,14-tetraoxatricosanoic acid methyl ester, 5,8,11,14-tetraoxatricosanoic acid ethyl ester, 5,8,11,14-tetraoxatricosanoic acid propyl ester, 5,8,11,14-tetraoxatricosanoic acid isopropyl ester, 5,8,11,14-tetraoxatricosanoic acid butyl ester, 5,8,11,14-tetraoxatricosanoic acid isobutyl ester, 5,8,11,14-tetraoxatricosanoic acid amyl ester, 5,8,11,14-tetraoxatricosanoic acid isoamyl ester, 5,8,11,14-tetraoxatricosanoic acid hexyl ester, 5,8,11,14-tetraoxatricosanoic acid cyclohexyl ester, 5,8,11,14-tetraoxatricosanoic acid methylhexyl ester, 5,8,11,14-tetraoxatricosanoic acid heptyl ester, 5,8,11,14-tetraoxatricosanoic acid methylheptyl ester, 5,8,11,14-tetraoxatricosanoic acid octyl ester, 5,8,11,14-tetraoxatricosanoic acid 2-ethylhexyl ester, 5,8,11,14-tetraoxatricosanoic acid nonyl ester, 5,8,11,14-tetraoxatricosanoic acid isononyl ester, 5,8,11,14-tetraoxatricosanoic acid 3,5,5-trimethylhexyl ester, 5,8,11,14-tetraoxatricosanoic acid decyl ester, 5,8,11,14-tetraoxatricosanoic acid isodecyl ester, 5,8,11,14-tetraoxatricosanoic acid dodecyl ester, 5,8,11,14-tetraoxatricosanoic acid tetradecyl ester, 5,8,11,14-tetraoxatricosanoic acid hexadecyl ester, 5,8,11,14-tetraoxatricosanoic acid 2-butyloctyl ester, 5,8,11,14-tetraoxatricosanoic acid 2-hexyldecyl ester, 5,8,11,14-tetraoxatricosanoic acid octadecyl ester, 5,8,11,14-tetraoxatricosanoic acid isooctadecyl ester, 5,8,11,14-tetraoxatetracosanoic acid methyl ester, 5,8,11,14-tetraoxatetracosanoic acid ethyl ester, 5,8,11,14-tetraoxatetracosanoic acid propyl ester, 5,8,11,14-tetraoxatetracosanoic acid isopropyl ester, 5,8,11,14-tetraoxatetracosanoic acid butyl ester, 5,8,11,14-tetraoxatetracosanoic acid isobutyl ester, 5,8,11,14-tetraoxatetracosanoic acid amyl ester, 5,8,11,14-tetraoxatetracosanoic acid isoamyl ester, 5,8,11,14-tetraoxatetracosanoic acid hexyl ester, 5,8,11,14-tetraoxatetracosanoic acid cyclohexyl ester, 5,8,11,14-tetraoxatetracosanoic acid methylhexyl ester, 5,8,11,14-tetraoxatetracosanoic acid heptyl ester, 5,8,11,14-tetraoxatetracosanoic acid methylheptyl ester, 5,8,11,14-tetraoxatetracosanoic acid octyl ester, 5,8,11,14-tetraoxatetracosanoic acid 2-ethylhexyl ester, 5,8,11,14-tetraoxatetracosanoic acid nonyl ester, 5,8,11,14-tetraoxatetracosanoic acid isononyl ester, 5,8,11,14-tetraoxatetracosanoic acid 3,5,5-trimethylhexyl ester, 5,8,11,14-tetraoxatetracosanoic acid decyl ester, 5,8,11,14-tetraoxatetracosanoic acid isodecyl ester, 5,8,11,14-tetraoxatetracosanoic acid dodecyl ester, 5,8,11,14-tetraoxatetracosanoic acid tetradecyl ester, 5,8,11,14-tetraoxatetracosanoic acid hexadecyl ester, 5,8,11,14-tetraoxatetracosanoic acid 2-butyloctyl ester, 5,8,11,14-tetraoxatetracosanoic acid 2-hexyldecyl ester, 5,8,11,14-tetraoxatetracosanoic acid octadecyl ester, 5,8,11,14-tetraoxatetracosanoic acid isooctadecyl ester, 5,8,11,14-tetraoxapentacosanoic acid methyl ester, 5,8,11,14-tetraoxapentacosanoic acid ethyl ester, 5,8,11,14-tetraoxapentacosanoic acid propyl ester, 5,8,11,14-tetraoxapentacosanoic acid isopropyl ester, 5,8,11,14-tetraoxapentacosanoic acid butyl ester, 5,8,11,14-tetraoxapentacosanoic acid isobutyl ester, 5,8,11,14-tetraoxapentacosanoic acid amyl ester, 5,8,11,14-tetraoxapentacosanoic acid isoamyl ester, 5,8,11,14-tetraoxapentacosanoic acid hexyl ester, 5,8,11,14-tetraoxapentacosanoic acid cyclohexyl ester, 5,8,11,14-tetraoxapentacosanoic acid methylhexyl ester, 5,8,11,14-tetraoxapentacosanoic acid heptyl ester, 5,8,11,14-tetraoxapentacosanoic acid methylheptyl ester, 5,8,11,14-tetraoxapentacosanoic acid octyl ester, 5,8,11,14-tetraoxapentacosanoic acid 2-ethylhexyl ester, 5,8,11,14-tetraoxapentacosanoic acid nonyl ester, 5,8,11,14-tetraoxapentacosanoic acid isononyl ester, 5,8,11,14-tetraoxapentacosanoic acid 3,5,5-trimethylhexyl ester, 5,8,11,14-tetraoxapentacosanoic acid decyl ester, 5,8,11,14-tetraoxapentacosanoic acid isodecyl ester, 5,8,11,14-tetraoxapentacosanoic acid dodecyl ester, 5,8,11,14-tetraoxapentacosanoic acid tetradecyl ester, 5,8,11,14-tetraoxapentacosanoic acid hexadecyl ester, 5,8,11,14-tetraoxapentacosanoic acid 2-butyloctyl ester, 5,8,11,14-tetraoxapentacosanoic acid 2-hexyldecyl ester, 5,8,11,14-tetraoxapentacosanoic acid octadecyl ester, 5,8,11,14-tetraoxapentacosanoic acid isooctadecyl ester, 5,8,11,14-tetraoxahexacosanoic acid methyl ester, 5,8,11,14-tetraoxahexacosanoic acid ethyl ester, 5,8,11,14-tetraoxahexacosanoic acid propyl ester, 5,8,11,14-tetraoxahexacosanoic acid isopropyl ester, 5,8,11,14-tetraoxahexacosanoic acid butyl ester, 5,8,11,14-tetraoxahexacosanoic acid isobutyl ester, 5,8,11,14-tetraoxahexacosanoic acid amyl ester, 5,8,11,14-tetraoxahexacosanoic acid isoamyl ester, 5,8,11,14-tetraoxahexacosanoic acid hexyl ester, 5,8,11,14-tetraoxahexacosanoic acid cyclohexyl ester, 5,8,11,14-tetraoxahexacosanoic acid methylhexyl ester, 5,8,11,14-tetraoxahexacosanoic acid heptyl ester, 5,8,11,14-tetraoxahexacosanoic acid methylheptyl ester, 5,8,11,14-tetraoxahexacosanoic acid octyl ester, 5,8,11,14-tetraoxahexacosanoic acid 2-ethylhexyl ester, 5,8,11,14-tetraoxahexacosanoic acid nonyl ester, 5,8,11,14-tetraoxahexacosanoic acid isononyl ester, 5,8,11,14-tetraoxahexacosanoic acid 3,5,5-trimethylhexyl ester, 5,8,11,14-tetraoxahexacosanoic acid decyl ester, 5,8,11,14-tetraoxahexacosanoic acid isodecyl ester, 5,8,11,14-tetraoxahexacosanoic acid dodecyl ester, 5,8,11,14-tetraoxahexacosanoic acid tetradecyl ester, 5,8,11,14-tetraoxahexacosanoic acid hexadecyl ester, 5,8,11,14-tetraoxahexacosanoic acid 2-butyloctyl ester, 5,8,11,14-tetraoxahexacosanoic acid 2-hexyldecyl ester, 5,8,11,14-tetraoxahexacosanoic acid octadecyl ester, 5,8,11,14-tetraoxahexacosanoic acid isooctadecyl ester, and the like.

The compound of the present invention needs only to have a kinetic viscosity (v) at 40° C. (hereinafter also referred to as "40° C. kinetic viscosity (v)" or "40° C. kinetic viscosity") of 4 mm$^2$/s to 30 mm$^2$/s. A compound having a 40° C. kinetic viscosity in the above range is suitable for a base oil for a lubricant, particularly a base oil for a bearing lubricant and a base oil for a freezer oil. The 40° C. kinetic viscosity is preferably 4 mm$^2$/s to 20 mm$^2$/s, further preferably 6 mm$^2$/s to 15 mm$^2$/s. A lubricant containing as a base oil the compound having the 40° C. kinetic viscosity in the above range can be particularly excellent in lubricity and energy-saving.

The compound of the present invention is preferably such that (i) in the general formula (1), m is an integer of 10 to 14, n is an integer of 1 to 12, p is 2, and 11≤n+m≤26 is satisfied, and (ii) the 40° C. kinetic viscosity (v) satisfies 4 mm$^2$/s≤v≤20 mm$^2$/s. In particular, the compound of the present invention is more preferably (i) a compound where m, n and p are 12, 8, and 2, respectively, in the general formula (1), (ii) a compound where m, n and p are 14, 8, and 2, respectively, in the general formula (1), or (iii) a compound where m, n and p are 10, 8, and 2, respectively, in the general formula (1).

The compound of the present invention is preferably such that (i) in the general formula (1), m is an integer of 1 to 14, n is an integer of 1 to 12, p is 1, and 5≤n+m≤26 is satisfied, and (ii) the 40° C. kinetic viscosity (v) satisfies 4 mm²/s≤v≤20 mm²/s.

The compound of the present invention is preferably such that (i) in the general formula (1), m is an integer of 1 to 18, n is an integer of 1 to 12, p is 3, and 2≤n+m≤30 is satisfied, and (ii) the 40° C. kinetic viscosity (v) satisfies 4 mm²/s≤v≤30 mm²/s.

Of the compound of the present invention, a compound having (i) a viscosity index of preferably not less than 160, more preferably not less than 180 and (ii) a solidification temperature of preferably not higher than −10° C., more preferably not higher than −20° C. is more suitable for a base oil for a lubricant, particularly a base oil for a bearing lubricant and a base oil for a freezer oil. A lubricant containing as a base oil a compound whose viscosity index and solidification temperature fall within the respective ranges can be particularly excellent in low-temperature fluidity.

Of the compound of the present invention, a compound having (i) an amount of evaporation of preferably not more than 20 wt %, more preferably not more than 10 wt % and (ii) an acid value of preferably not more than 1 mgKOH/g, more preferably not more than 0.5 mgKOH/g is more suitable for a base oil for a lubricant, particularly a base oil for a bearing lubricant and a base oil for a freezer oil. A lubricant containing as a base oil a compound whose amount of evaporation and acid value fall within the respective ranges can be particularly excellent in heat resistance.

In a case where a lubricant contains as a base oil a compound, of the compound of the present invention, which has (i) a 40° C. kinetic viscosity of 6 mm²/s to 15 mm²/s, (ii) a viscosity index of not less than 160, (iii) a solidification temperature of not higher than −15° C., (iv) an amount of evaporation of not more than 15 wt %, and (v) an acid value of not more than 0.5 mgKOH/g, the lubricant can be well balanced in energy-saving, heat resistance and low-temperature fluidity which are necessary for a bearing lubricant. In a case where a lubricant contains as a base oil a compound, of the compound of the present invention, which has (i) a 40° C. kinetic viscosity of 4 mm²/s to 30 mm²/s, (ii) a viscosity index of not less than 160, (iii) a solidification temperature of not higher than −10° C., (iv) an amount of evaporation of not more than 20 wt %, and (v) an acid value of not more than 0.5 mgKOH/g, the lubricant can be well balanced in energy-saving, heat resistance and low-temperature fluidity which are necessary for a freezer oil.

Note that the "40° C. kinetic viscosity", the "viscosity index", the "solidification temperature", the "amount of evaporation", and the "acid value" in this specification mean values measured according to methods described in Examples (later described).

The following description will discuss an example of a method of synthesizing the compound of the present invention.

<Method of Synthesizing Compound>

The compound represented by the general formula (1) can be obtained by, for example, esterification reaction of and etherification reaction of γ-butyrolactone and an alcohol which is represented by the following general formula (2). The obtained compound represented by the general formula (1) and an alcohol represented by the following general formula (3) are subjected to transesterification reaction, so that the compound represented by the general formula (1) can be adjusted to have a desired molecular structure in the range represented by the general formula (1).

$$C_nH_{2n+1}\text{-}(O\text{---}CH_2CH_2)_p\text{-}O\text{---}H \qquad (2)$$

$$H\text{---}O\text{---}C_mH_{2m+1} \qquad (3)$$

where O represents an oxygen atom, C represents a carbon atom, H represents a hydrogen atom, p is an integer of 1 to 3, m is an integer of 1 to 18, n is an integer of 1 to 12, and 2≤n+m≤30 is satisfied.

Note that the method of synthesizing the compound of the present invention is not limited to the foregoing method.

After the transesterification reaction is sufficiently carried out, a known method (e.g., reduced-pressure distillation etc.) is performed to purify a product as appropriate. This makes it possible to use the compound represented by the general formula (1) as a base oil of a lubricant.

[2. Lubricant in Accordance with the Present Invention]

The lubricant in accordance with the present invention (hereinafter also referred to as "lubricant of the present invention") is characterized in containing the compound of the present invention. That is, the lubricant of the present invention is a lubricant containing the compound of the present invention as a base oil. Note that the compound of the present invention has been described in the foregoing [1. Compound in accordance with the present invention], and therefore description of the compound of the present invention is omitted here.

The lubricant of the present invention contains the compound of the present invention in an amount of preferably 50 wt % to 97 wt %, more preferably 80 wt % to 97 wt %, most preferably 95 wt % to 97 wt % relative to the total weight of the lubricant. The lubricant of the present invention containing the compound of the present invention within the above range can be low in viscosity (excellent in energy-saving) and excellent in heat resistance and low-temperature fluidity as compared to traditional lubricants. The lubricant of the present invention may contain a single kind of the compound of the present invention, or may contain plural kinds of the compound of the present invention in combination.

The lubricant of the present invention preferably contains as the compound of the present invention a compound serving as a base oil and being such that (i) in the general formula (1), m is an integer of 10 to 14, n is an integer of 1 to 12, p is 2, and 11≤n+m≤26 is satisfied, and (ii) the 40° C. kinetic viscosity (v) satisfies 4 mm²/s≤v≤20 mm²/s. In particular, the lubricant of the present invention more preferably contains, as the base oil, (i) a compound where m, n and p are 12, 8, and 2, respectively, in the general formula (1), (ii) a compound where m, n and p are 14, 8, and 2, respectively, in the general formula (1), or (iii) a compound where m, n and p are 10, 8, and 2, respectively, in the general formula (1). This lubricant can be excellent in energy-saving, heat resistance, and low-temperature fluidity which are well balanced, as compared to traditional lubricants.

The lubricant of the present invention preferably contains as the compound of the present invention a compound serving as a base oil and being such that (i) in the general formula (1), m is an integer of 1 to 14, n is an integer of 1 to 12, p is 1, and 5≤n+m≤26 is satisfied, and (ii) the 40° C. kinetic viscosity (v) satisfies 4 mm²/s≤v≤20 mm²/s. This lubricant can be excellent in energy-saving, heat resistance, and low-temperature fluidity which are well balanced, as compared to traditional lubricants.

The lubricant of the present invention preferably contains as the compound of the present invention a compound serving as a base oil and being such that (i) in the general formula (1), m is an integer of 1 to 18, n is an integer of 1 to 12, p is 3, and $2 \leq n+m \leq 30$ is satisfied, and (ii) the 40° C. kinetic viscosity (v) satisfies 4 mm$^2$/s $\leq$ v $\leq$ 30 mm$^2$/s. This lubricant can be excellent in energy-saving, heat resistance, and low-temperature fluidity which are well balanced, as compared to traditional lubricants.

The lubricant of the present invention may contain, in addition to the compound of the present invention, (i) a hydrocarbon oil such as mineral oil, olefin polymer or alkylbenzene, or (ii) an oxygen atom-containing synthetic oil such as polyglycol, polyvinyl ether, ketone, polyphenyl ether, silicone, polysiloxane, perfluoroether, or ester or ether other than the compound of the present invention. The hydrocarbon oil or synthetic oil is preferably contained in an amount of 1 wt % to 50 wt % relative to the total weight of the lubricant. The lubricant of the present invention containing the hydrocarbon oil or synthetic oil in the above amount can have a low viscosity (excellent energy-saving) and excellent heat resistance and low-temperature fluidity in a well-balanced manner, as compared to traditional lubricants.

The lubricant of the present invention may further contain various additives in addition to the compound of the present invention which serves as a base oil, so as to achieve better practical properties. Examples of the additives include, for example, phenolic antioxidants, amine antioxidants, sulfuric antioxidants, phosphorus antioxidants, epoxy compounds (which serve as hydrolysis resistance improvers), benzotriazole derivatives (which serve as metal deactivators), zinc dithiophosphate (which serves as an extreme-pressure agent), and the like.

The lubricant of the present invention can have better practical properties by containing at least one selected from these additives in an amount of 0.01 wt % to 3 wt % relative to the total weight of the lubricant.

Examples of the "phenolic antioxidants" include, for example, 2,6-di-t-butylphenol, 2,6-di-t-butyl-4-methylphenol, 2,6-di-t-butyl-4-ethylphenol, 2,6-di-t-butyl-4-n-butylphenol (ethyl 744), 4,4'-methylenebis(2,6-di-t-butylphenol), 2,2'-thiobis(4-methyl-6-t-butylphenol), and the like. Examples of the "amine antioxidants" include, for example, N-phenyl-α-naphthylamine, p,p'-dioctyldiphenylamine, and the like. Examples of the "sulfuric antioxidants" include, for example, phenothiazine, and the like.

Other usable antioxidants, anti-wearing agents, and extreme-pressure agents include: for example, phosphorous compounds such as (i) phosphates such as tricresyl phosphate, cresyl diphenyl phosphate, alkyl phenyl phosphates, tributyl phosphate, and dibutyl phosphate, (ii) phosphites such as tributyl phosphite, triphenyl phosphite, and tricresyl phosphite, and (iii) amine salts of those listed above; sulfuric compounds such as (i) sulfurized fatty acids such as sulfurized oil and sulfurized oleic acid, (ii) dibenzyldisulfide, (iii) sulfurized olefin, and (iv) dialkyl disulfide; organometallic compounds such as Zn-dialkyl dithiophosphate, Zn-dialkyl dithiocarbamate, Mo-dialkyl dithiophosphate, and Mo-dialkyl dithiocarbamate; and the like.

The lubricant of the present invention has a 40° C. kinetic viscosity of preferably 4 mm$^2$/s to 30 mm$^2$/s, more preferably 4 mm$^2$/s to 20 mm$^2$/s, still more preferably 6 mm$^2$/s to 15 mm$^2$/s. The lubricant having the 40° C. kinetic viscosity within the above range can be particularly excellent in lubricity and energy-saving.

The lubricant of the present invention has (i) a viscosity index of preferably not less than 160, more preferably not less than 180, and (ii) a solidification temperature of preferably not higher than −10° C., more preferably not higher than −20° C. In this case, the lubricant of the present invention can be particularly excellent in low-temperature fluidity.

The lubricant of the present invention has (i) an amount of evaporation of preferably not more than 20 wt %, more preferably not more than 10 wt % and (ii) an acid value of preferably not more than 1 mgKOH/g, more preferably not more than 0.5 mgKOH/g. In this case, the lubricant of the present invention can be particularly excellent in heat resistance.

In a case where the lubricant of the present invention has a 40° C. kinetic viscosity of 6 mm$^2$/s to 15 mm$^2$/s, a viscosity index of not less than 160, a solidification temperature of not higher than −15° C., an amount of evaporation of not more than 15 wt %, and an acid value of not more than 0.5 mgKOH/g, the lubricant of the present invention can be well balanced in energy-saving, heat resistance, and low-temperature fluidity which are necessary for a bearing lubricant. In a case where the 40° C. kinetic viscosity is 4 mm$^2$/s to 30 mm$^2$/s, the viscosity index is not less than 160, the solidification temperature is not higher than −10° C., the amount of evaporation is not more than 20 wt %, and the acid value is not more than 0.5 mgKOH/g, the lubricant of the present invention can be well balanced in energy-saving, heat resistance, and low-temperature fluidity which are necessary for a freezer oil.

As such, the lubricant of the present invention can have a low viscosity (excellent energy-saving) and excellent heat resistance and low-temperature fluidity in a well-balanced manner, as compared to traditional lubricants. It is therefore possible to (i) achieve long-term stability and durability, etc. even in a case where a bearing is rotated at high speed and (ii) improve energy-saving, by using the lubricant of the present invention as a working fluid for lubricating the bearing. It is further possible to provide a bearing usable in a wide range of temperatures. On this account, the lubricant of the present invention can be effectively used as a lubricant for a bearing provided in a rotating device etc. of an electronic device (such as an audio-visual device, a server or a personal computer) which has been required to decrease in size and weight and increase in memory capacity and information processing speed.

The lubricant of the present invention can be used as a lubricant for any bearing to be lubricated with use of the lubricant. For example, the lubricant of the present invention can be suitably used as a lubricant for any bearing that includes a shaft member and a bearing member (sleeve member) and is arranged such that (i) the shaft member and the bearing member are rotatably fitted with each other via a minute gap between them, (ii) a working fluid (lubricant) is contained in the minute gap so as to form a lubricating film and (iii) the shaft member and the bearing member relatively slide via the lubricating film. This bearing is generally called a "slide bearing".

The lubricant of the present invention can be suitably used also as a lubricant for a fluid bearing (fluid dynamic bearing or static pressure bearing) or an impregnated bearing (also called "oil-impregnated bearing").

The lubricant of the present invention can also be used to produce a grease. It is possible to produce a grease by using the lubricant of the present invention as a grease base oil. Such a grease will be described later.

The lubricant of the present invention can also be used as a lubrication oil (freezer oil) for a freezer. This freezer oil will be described later.

[3. Bearing in Accordance with the Present Invention]

The bearing in accordance with the present invention (hereinafter also referred to as "bearing of the present invention") is not limited to a particular configuration, provided that the bearing is to be lubricated with use of the lubricant of the present invention. Note that "to be lubricated with use of the lubricant of the present invention" intends that members facing each other via the lubricant of the present invention relatively slide via the lubricant of the present invention.

Examples of the bearing include, for example, a fluid dynamic bearing and an impregnated bearing. Note that the lubricant of the present invention has been described in the foregoing [2. Lubricant in accordance with the present invention], and therefore description of the lubricant of the present invention is omitted here.

The "fluid dynamic bearing" is not limited to a particular configuration, provided that it is a publicly known fluid dynamic bearing which (i) includes a shaft member (or a thrust plate) and a sleeve member but does not have a mechanism such as a ball bearing and (ii) is arranged such that: the shaft member (or thrust plate) and the sleeve member are rotatably fitted with each other via a minute gap between them; a working fluid (lubricant) is contained in the minute gap so as to form a lubricating film; and the shaft member (or thrust plate) and the sleeve member are held so as not to be in direct contact with each other via the lubricating film.

Of such fluid dynamic bearings, the following are particularly called "fluid dynamic bearings": a fluid dynamic bearing in which a shaft member and/or a sleeve member have/has a dynamic pressure generating groove(s), and the shaft member is supported by dynamic pressure; a fluid dynamic bearing which includes a thrust plate so that dynamic pressure is generated in a direction perpendicular to a rotation axis of a shaft member; and the like. The bearing of the present invention also encompasses such fluid dynamic bearings.

In the fluid dynamic bearings described above, no dynamic pressure is generated while the shaft member (or thrust plate) is not rotating. Therefore, while the shaft member (or thrust plate) is not rotating, the sleeve member and the shaft member (or thrust plate) are partly or fully in contact with each other. On the other hand, while the shaft member (or thrust plate) is rotating, dynamic pressure is generated by the rotation, and thus the sleeve member and the shaft member (or thrust plate) separate from each other. That is, in the fluid dynamic bearings, the sleeve member and the shaft member (or thrust plate) constantly repeat contacting with and separating from each other. According to traditional fluid dynamic bearings, (i) metal wear may occur between a sleeve member and a shaft member (or thrust plate) or (ii) seizure may occur because the sleeve member and the shaft member (or thrust plate) temporarily contact with each other while the shaft member (or thrust plate) is rotating. Furthermore, since traditional fluid dynamic bearings are likely to accumulate static electricity, important electronic components such as a magnetic disk may suffer electrostatic destruction. On the other hand, the fluid dynamic bearings in accordance with the present invention are lubricated with use of the lubricant of the present invention. This reduces the possibility of such metal wear and seizure, and also reduces the likelihood that static electricity is accumulated between the sleeve member and the shaft member (or thrust plate).

The "impregnated bearing" is not limited to a particular configuration, provided that it is a publicly known impregnated bearing (oil-impregnated bearing) which includes a porous shaft member that is (i) made of sintered metal, synthetic resin or the like and (ii) impregnated with the lubricant of the present invention.

In traditional impregnated bearings, (i) metal wear may occur between a sleeve member and a shaft member or (ii) seizure may occur because the sleeve member and the shaft member temporarily contact with each other while the shaft member is rotating. Furthermore, since the traditional impregnated bearings are likely to accumulate static electricity, important electronic components such as a magnetic disk may suffer electrostatic destruction. On the other hand, the impregnated bearing in accordance with the present invention is lubricated with use of the lubricant of the present invention. This reduces the possibility of such metal wear and seizure, and also reduces the likelihood that static electricity is accumulated between the sleeve member and the shaft member.

As described earlier, the lubricant of the present invention can have a low viscosity (excellent energy-saving), and excellent heat resistance and low-temperature fluidity in a well-balanced manner, as compared to traditional lubricants. Accordingly, the bearing of the present invention, which is lubricated with use of the lubricant of the present invention as a working fluid, can be used as a bearing that (i) achieves long-term stability and durability, etc. even in a case where the bearing is rotated at high speed and (ii) is excellent in energy-saving. In addition, the bearing of the present invention can be used as a bearing usable in a wide range of temperatures. As such, the bearing of the present invention can be effectively used as a bearing for use in a rotating device etc. of an electronic device, such as an audio-visual device, a server or a personal computer, which has been required to decrease in size and weight and increase in memory capacity and information processing speed.

[4. Method in Accordance with the Present Invention of Lubricating Bearing]

A method in accordance with the present invention of lubricating a bearing is characterized in lubricating the bearing of the present invention with use of the lubricant of the present invention. Note that the lubricant of the present invention and the bearing of the present invention have been described in the foregoing [2. Lubricant in accordance with the present invention] and [3. Bearing in accordance with the present invention], respectively, and therefore descriptions of the lubricant of the present invention and the bearing of the present invention are omitted here.

As has been described, the lubricant of the present invention can have a low viscosity (excellent energy-saving), and excellent heat resistance and low-temperature fluidity in a well-balanced manner, as compared to traditional lubricants. Accordingly, by applying to a bearing, in particular, a fluid dynamic bearing or an impregnated bearing, the lubricant of the present invention as a working fluid for lubricating the bearing, it is possible to achieve long-term stability and durability, etc. even in a case where the bearing is rotated at high speed, and thus possible to increase the lifetime of the bearing. It is also possible to improve energy-saving of the bearing. It is furthermore possible to provide a bearing usable in a wide range of temperatures.

[5. Motor in Accordance with the Present Invention]

The motor in accordance with the present invention is not limited to a particular configuration, provided that it includes the bearing of the present invention. Note that the bearing of the present invention has been described in the foregoing [3. Bearing in accordance with the present invention], and therefore description of the bearing of the present invention is omitted here.

Examples of the motor in accordance with the present invention include those provided in publicly known electronic devices such as servers, personal computers, audio devices, visual devices, and car navigation systems.

The motor in accordance with the present invention includes the bearing which has been lubricated with use of the lubricant of the present invention. The motor in accordance with the present invention, therefore, is less likely to suffer metal wear and seizure and less likely to accumulate static electricity between the sleeve member and the shaft member, as compared to traditional motors. As such, the motor in accordance with the present invention achieves long-term stability and durability, etc. even in a case where the bearing is rotated at high speed, and thus increases the lifetime of the motor. Furthermore, the motor in accordance with the present invention can be used as a motor particularly excellent in energy-saving in the case where the bearing is rotated at high speed, as compared to the traditional motors. The motor in accordance with the present invention can also be used as a motor usable in a wide range of temperatures, as compared to the traditional motors.

[6. Grease in Accordance with the Present Invention]

The grease in accordance with the present invention is characterized in containing the lubricant of the present invention. Note that the lubricant of the present invention has been described in the foregoing [2. Lubricant in accordance with the present invention], and therefore description of the lubricant of the present invention is omitted here.

The grease in accordance with the present invention contains the lubricant of the present invention in an amount of preferably 50 wt % to 97 wt %, more preferably 95 wt % to 97 wt % relative to the total weight of the grease.

The grease in accordance with the present invention may be solid or semisolid at room temperature.

The grease in accordance with the present invention contains a consistency increasing agent in an amount that is required for a desired consistency to be achieved. Usually, the consistency increasing agent is contained in an amount of, for example, 10 wt % to 40 wt % relative to the total weight of the grease.

The "consistency increasing agent" may be one that is usually used in grease. Examples of the consistency increasing agent include, but not limited to, lithium soap, calcium soap, sodium soap, aluminum soap and the like.

The grease in accordance with the present invention may further contain additives such as antioxidants, extreme-pressure agents, and/or corrosion inhibitors according to need. Each of these additives, when contained in the grease, accounts for 0.1 wt % to 3 wt % of the total weight of the grease. This makes it possible to achieve better practical properties of the grease.

The grease in accordance with the present invention is not particularly limited as to its application, but it is suitable for use as a grease for a bearing, particularly as a grease for a fluid dynamic bearing or a grease for an impregnated bearing.

A method of producing the grease in accordance with the present invention is not particularly limited. The grease in accordance with the present invention can be produced by a typical grease production method.

Since the grease in accordance with the present invention contains the lubricant of the present invention as a base oil, the grease can be used as a grease which more certainly meets all the properties such as energy-saving, heat resistance and low-temperature fluidity in a well-balanced manner, as compared to traditional greases.

[7. Freezer Oil in Accordance with the Present Invention]

The freezer oil in accordance with the present invention (hereinafter also referred to as "freezer oil of the present invention") is characterized in containing the compound of the present invention. Note that the compound of the present invention has been described in the foregoing [1. Compound in accordance with the present invention], and therefore description of the compound of the present invention is omitted here.

Since the freezer oil in accordance with the present invention contains the compound of the present invention as a base oil, the freezer oil in accordance with the present invention can be used as a freezer oil which (i) is excellent in energy-saving, heat resistance, and low-temperature fluidity and (ii) more certainly meets all these properties in a well-balanced manner, as compared to traditional freezer oils. Since the compound of the present invention has a moderate compatibility with or solubility to a hydrocarbon coolant, the freezer oil of the present invention containing this compound can be used as a freezer oil particularly excellent in lubricity, stability and the like.

In the freezer oil in accordance with the present invention, the amounts of unreacted and residual acid and hydroxyl group which are derived from the compound of the present invention are not particularly limited. It is, however, preferable that a carboxyl group and a hydroxyl group do not remain in the freezer oil in accordance with the present invention. In a case where a large amount of carboxyl group remains, an unfavorable phenomenon sometimes occurs in which, for example, the carboxyl group reacts with a metal used inside a freezer, so that a metal soap etc. is generated and precipitated. The compound of the present invention contained in the freezer oil in accordance with the present invention therefore has an acid value of preferably not more than 3 mgKOH/g, more preferably not more than 0.5 mgKOH/g. In a case where the compound of the present invention contains a large amount of residual hydroxyl group, an unfavorable phenomenon sometimes occurs in which, for example, ester becomes cloudy at low temperature, so that a capillary device of a freezing cycle is blocked. The compound of the present invention contained in the freezer oil in accordance with the present invention therefore has a hydroxyl value of preferably not more than 3 mgKOH/g, more preferably not more than 0.5 mgKOH/g.

The freezer oil of the present invention contains the compound of the present invention in an amount of preferably 50 wt % to 97 wt %, more preferably 80 wt % to 97 wt % relative to the total weight of the freezer oil. The freezer oil of the present invention containing the compound of the present invention in the foregoing amount can be used as (i) a freezer oil low in viscosity (excellent in energy-saving) and excellent in heat resistance and low-temperature fluidity, as compared to traditional freezer oils and (ii) a freezer oil particularly excellent in lubricity, stability and the like. The freezer oil of the present invention may contain a single kind of the compound of the present invention or plural kinds of the compound of the present invention in combination.

The freezer oil of the present invention may be mixed as appropriate with a lubrication oil such as polyalkylene glycol, alkylbenzene, mineral oil, etc. within a range which allows the freezer oil of the present invention to function as a freezer oil. The freezer oil of the present invention may have appropriately added thereto an additive(s) such as an antioxidant, an anti-wearing agent, and/or an epoxy compound which are/is contained in traditional freezer oils. The additive(s) preferably account(s) for not more than 3 wt % relative to the total weight of the freezer oil of the present invention.

A method of producing the freezer oil in accordance with the present invention is not particularly limited. The freezer oil in accordance with the present invention can be produced by a typical method of producing a freezer oil.

Since the compound of the present invention has a moderate compatibility with or solubility to a hydrocarbon coolant, the freezer oil of the present invention mainly containing the compound of the present invention, when used as a freezer oil for a freezer that uses a hydrocarbon coolant, can show an appropriate compatibility with or solubility to a coolant within a wide range of temperatures from low temperature to high temperature, and can remarkably improve its lubricity and thermal stability.

The freezer oil of the present invention can be used as a lubrication oil for a freezer which uses as a coolant (i) a $C_1$ to $C_5$ lower hydrocarbon such as ethane, propane, butane or isobutene or (ii) a new hydrogen-containing chlorofluorocarbon coolant such as difluoromethane (R-32) or tetrafluoroethane (R-134 or R-134a). Particularly, the freezer oil of the present invention can be suitably used as a lubrication oil for a high cooling efficiency freezing system, particularly a freezer having a high-pressure compressor such as a rotary compressor, the system (i) having a compressor, a condensing device, a squeezer (a coolant flow control section of an expansion valve, a capillary tube or the like), an evaporator, etc. and (ii) circulating a coolant among these devices.

The present invention is not limited to the embodiments, but can be altered by a skilled person in the art within the scope of the claims. An embodiment derived from a proper combination of technical means each disclosed in a different embodiment is also encompassed in the technical scope of the present invention.

EXAMPLES

The following description will more specifically discuss the present invention on the basis of Examples. Note, however, that the present invention is not limited to Examples.

Examples 1 Through 18

Evaluated were the molecular weight, kinetic viscosity, viscosity index, acid value, state at 20° C., low-temperature fluidity (solidification temperature), lubricity and heat resistance of a compound represented by the general formula (1).

Compounds of Examples 1 through 18 were synthesized as the compound represented by the general formula (1). These compounds were synthesized according to the foregoing method described in the foregoing [1. Compound in accordance with the present invention]. Table 1 shows the compounds of Examples 1 through 18.

TABLE 1

| Name of Compound | | Symbol in general formula (1) | | |
|---|---|---|---|---|
| | | n | m | p |
| Ex.1 | 5,8-dioxatetradecanoic acid n-butyl ester | 6 | 4 | 1 |
| Ex.2 | 5,8-dioxatetradecanoic acid isoamyl ester | 6 | 5 | 1 |
| Ex.3 | 5,8-dioxatetradecanoic acid n-hexyl ester | 6 | 6 | 1 |
| Ex.4 | 5,8-dioxatetradecanoic acid 2-ethylhexyl ester | 6 | 8 | 1 |
| Ex.5 | 5,8-dioxatetradecanoic acid n-dodecyl ester | 6 | 12 | 1 |
| Ex.6 | 5,8-dioxatetradecanoic acid 2-butyloctyl ester | 6 | 12 | 1 |
| Ex.7 | 10-ethyl-5,8-dioxatetradecanoic acid n-octyl ester | 8 | 8 | 1 |
| Ex.8 | 10-ethyl-5,8-dioxatetradecanoic acid n-decyl ester | 8 | 10 | 1 |
| Ex.9 | 10-ethyl-5,8-dioxatetradecanoic acid n-dodecyl ester | 8 | 12 | 1 |
| Ex.10 | 10-ethyl-5,8-dioxatetradecanoic acid n-tetradecyl ester | 8 | 14 | 1 |
| Ex.11 | 5,8,11-trioxadodecanoic acid 2-butyloctyl ester | 1 | 12 | 2 |
| Ex.12 | 5,8,11-trioxadodecanoic acid 2-hexyldecyl ester | 1 | 16 | 2 |
| Ex.13 | 5,8,11-trioxaheptadecanoic acid n-dodecyl ester | 6 | 12 | 2 |
| Ex.14 | 13-ethyl-5,8,11-trioxaheptadecanoic acid n-decyl ester | 8 | 10 | 2 |
| Ex.15 | 13-ethyl-5,8,11-trioxaheptadecanoic acid n-dodecyl ester | 8 | 12 | 2 |
| Ex.16 | 13-ethyl-5,8,11-trioxaheptadecanoic acid n-tetradecyl ester | 8 | 14 | 2 |
| Ex.17 | 5,8,11,14-tetraoxaoctadecanoic acid 2-ethylhexyl ester | 4 | 8 | 3 |
| Ex.18 | 5,8,11,14-tetraoxaoctadecanoic acid 2-butyloctyl ester | 4 | 12 | 3 |
| Com. Ex.10 | 5-oxatetradecanoic acid n-dodecyl ester | 9 | 12 | 0 |

Table 2 shows the results of the molecular weight, kinetic viscosity, viscosity index, acid value, state at 20° C., low-temperature fluidity (solidification temperature), and lubricity test of each of the compounds of Examples. Table 2 also shows the result of a heat resistance test in a case where a 2 wt % amine antioxidant (VANLUBE 81 manufactured by R.T.VANDERBILT CO., INC.) was mixed with each of the compounds of Examples.

Comparative Examples 1 Through 10

Compounds of Comparative Examples 1 through 10 traditionally used as lubrication oils etc. were synthesized by an existing method. These compounds were tested in the same manner as the compounds of Examples 1 through 18. Note that the compound of Comparative Example 10 is identical to a compound described in Japanese Patent Application Publication Tokukai No. 2012-56873 (Patent Literature 4). Table 1 shows the compound of Comparative Example 10.

<Evaluation Method>

Evaluation tests for kinetic viscosity, viscosity index, acid value, low-temperature fluidity (solidification temperature), lubricity, and heat resistance of each of the compounds were carried out in the following manners.

1) 40° C. kinetic viscosity: measured with use of a Cannon-Fenske viscometer in conformity to JIS K 2283
2) 100° C. kinetic viscosity: measured with use of a Cannon-Fenske viscometer in conformity to JIS K 2283
3) Viscosity index: calculated in conformity to JIS K 2283
4) Acid value: measured in conformity to JIS K 2501
5) Fluidity at low temperature (solidification temperature): 2 g of each of the compounds was put into a cylindrical glass container having an internal diameter of 18 mm and a height of 35 mm. The container was sealed, left at rest at a predetermined temperature for 12 hours in a cryostat, and then taken out from the cryostat. Fluidity in the container inclined immediately after being taken out was checked. A temperature at which no fluidity was found was regarded as a solidification temperature. Note that test was carried out at intervals of 5° C. from 0° C. to −40° C., and data was collected.

6) Lubricity test: a friction coefficient of to-and-fro sliding at 100° C. was measured with use of a ball-plate type friction tester (Tribo Tester) manufactured by Kyoshin Denki Seisakusho (Kyoshin Electric Mfg. Co., Ltd.). Used were (i) a ball whose material was high carbon chromium bearing steel (SUJ2) and whose diameter was 3/16 inch and (ii) a plate whose material was carbon tool steel (SK) and whose longitudinal length, lateral length and thickness were 18 mm, 28 mm and 1 mm, respectively. Test was carried out at a sliding speed of 5 mm per second under a vertical load of 100 g with use of 4 ml of each of the compounds.

7) Heat resistance test: 2 g of a lubricant was put into a cylindrical test container whose material was stainless steel (SUS 304), whose internal diameter was 20 mm, and whose height was 35 mm. The container was left at rest in a thermostat provided with a rotary table, the thermostat having a temperature set to a predetermined temperature. Evaporation loss was observed. A compound whose molecular weight was less than 380 was tested at 140° C. for 24 hours. A compound whose molecular weight was not less than 380 was tested at 180° C. for 18 hours.

TABLE 2

| | | | Ester | Kinetic viscosity (mm²/s) | |
|---|---|---|---|---|---|
| | Name of Compound | Molecular weight | structural formula | 40° C. | 100° C. |
| Ex. 1 | 5,8-dioxatetradecanoic acid n-butyl ester | 288 | See below | 4.59 | 1.66 |
| Ex. 2 | 5,8-dioxatetradecanoic acid isoamyl ester | 302 | See below | 5.60 | 1.96 |
| Ex. 3 | 5,8-dioxatetradecanoic acid n-hexyl ester | 316 | See below | 4.71 | 1.75 |
| Ex. 4 | 5,8-dioxatetradecanoic acid 2-ethylhexyl ester | 345 | See below | 5.35 | 1.87 |
| Ex. 5 | 5,8-dioxatetradecanoic acid n-dodecyl ester | 401 | See below | 8.46 | 2.73 |
| Ex. 6 | 5,8-dioxatetradecanoic acid 2-butyloctyl ester | 401 | See below | 7.69 | 2.34 |
| Ex. 7 | 10-ethyl-5,8-dioxatetradecanoic acid n-octyl ester | 373 | See below | 6.08 | 2.09 |
| Ex. 8 | 10-ethyl-5,8-dioxatetradecanoic acid n-decyl ester | 401 | See below | 7.49 | 2.42 |
| Ex. 9 | 10-ethyl-5,8-dioxatetradecanoic acid n-dodecyl ester | 429 | See below | 9.44 | 2.93 |
| Ex. 10 | 10-ethyl-5,8-dioxatetradecanoic acid n-tetradecyl ester | 457 | See below | 11.5 | 3.41 |
| Ex. 11 | 5,8,11-trioxadodecanoic acid 2-butyloctyl ester | 375 | See below | 6.98 | 2.22 |
| Ex. 12 | 5,8,11-trioxadodecanoic acid 2-hexyldecyl ester | 431 | See below | 10.18 | 2.84 |
| Ex. 13 | 5,8,11-trioxaheptadecanoic acid n-dodecyl ester | 445 | See below | 10.2 | 3.2 |
| Ex. 14 | 13-ethyl-5,8,11-trioxaheptadecanoic acid n-decyl ester | 445 | See below | 9.15 | 2.92 |
| Ex. 15 | 13-ethyl-5,8,11-trioxaheptadecanoic acid n-dodecyl ester | 473 | See below | 11.2 | 3.24 |
| Ex. 16 | 13-ethyl-5,8,11-trioxaheptadecanoic acid n-tetradecyl ester | 501 | See below | 13.4 | 3.77 |
| Ex. 17 | 5,8,11,14-tetraoxaoctadecanoic acid 2-ethylhexyl ester | 405 | See below | 7.81 | 2.51 |
| Ex. 18 | 5,8,11,14-tetraoxaoctadecanoic acid 2-butyloctyl ester | 461 | See below | 10.01 | 2.99 |
| Com. Ex. 1 | n-hexadecanoic acid methyl ester | 270 | See below | 4.07 | 1.64 |
| Com. Ex. 2 | n-octadecanoic acid ethyl ester | 313 | See below | 6.4 | 2.17 |
| Com. Ex. 3 | n-dodecanoic acid decyl ester | 341 | See below | 7.34 | 2.38 |
| Com. Ex. 4 | n-octadecanoic acid amyl ester | 355 | See below | 8.37 | 2.64 |
| Com. Ex. 5 | 2-ethylhexanoic acid n-hexadecyl ester | 369 | See below | 8.51 | 2.61 |
| Com. Ex. 6 | n-hexadecanoic acid 2-ethylhexyl ester | 369 | See below | 8.32 | 2.71 |
| Com. Ex. 7 | adipic acid di(2-ethylhexyl) ester | 371 | See below | 7.71 | 2.32 |
| Com. Ex. 8 | sebacic acid di(2-ethylhexyl) ester | 395 | See below | 11.6 | 3.20 |
| Com. Ex. 9 | 3-methyl-1,5-pentanediol di(n-undecanoate) ester | 455 | See below | 12.8 | 3.62 |
| Com. Ex. 10 | 5-oxatetradecanoic acid n-dodecyl ester | 399 | See below | 9.29 | 2.89 |

| | Viscosity index | Acid value (mgKOH/g) | State at 20 C. | Solidification temperature (C.) | Friction coefficient | Amount of evaporation (wt %) |
|---|---|---|---|---|---|---|
| Ex. 1 | — | 0.04 | Liquid | <−40 | — | — |
| Ex. 2 | — | 0.03 | Liquid | <−40 | — | — |
| Ex. 3 | — | 0.01 | Liquid | <−40 | — | 18 |
| Ex. 4 | — | 0.05 | Liquid | <−40 | — | 11.9 |
| Ex. 5 | 187 | 0.01 | Liquid | −15 | 0.065 | 9.6 |
| Ex. 6 | 125 | 0.01 | Liquid | <−40 | — | — |
| Ex. 7 | 162 | 0.03 | Liquid | <−40 | 0.064 | 6.9 |
| Ex. 8 | 161 | 0.00 | Liquid | <−40 | — | — |
| Ex. 9 | 182 | 0.02 | Liquid | −35 | 0.059 | 5.8 |
| Ex. 10 | 190 | 0.01 | Liquid | −25 | — | 3.3 |
| Ex. 11 | 133 | 0.03 | Liquid | <−40 | — | 7.0 |
| Ex. 12 | 130 | 0.15 | Liquid | <−40 | — | — |
| Ex. 13 | 193 | 0.00 | Liquid | −10 | 0.060 | 5.0 |
| Ex. 14 | 194 | 0.00 | Liquid | <−40 | — | 7.0 |
| Ex. 15 | 169 | 0.00 | Liquid | −40 | 0.067 | 3.0 |
| Ex. 16 | 189 | 0.00 | Liquid | −20 | — | 2.5 |
| Ex. 17 | 167 | 0.02 | Liquid | <−40 | — | — |
| Ex. 18 | 168 | 0.02 | Liquid | <−40 | 0.063 | 5.4 |
| Com. Ex. 1 | — | — | Solid | 31 | — | — |
| Com. Ex. 2 | 156 | — | Solid | 30 | — | — |
| Com. Ex. 3 | 157 | — | Solid | 22 | — | — |
| Com. Ex. 4 | 166 | — | Solid | 30 | — | — |
| Com. Ex. 5 | 151 | — | Liquid | −5 | — | — |
| Com. Ex. 6 | 190 | — | Liquid | 0 | — | — |

TABLE 2-continued

| | | | | | | |
|---|---|---|---|---|---|---|
| Com. Ex. 7 | 113 | 0.00 | Liquid | <−40 | 0.072 | 7.0 |
| Com. Ex. 8 | 149 | 0.00 | Liquid | <−40 | — | 9.1 |
| Com. Ex. 9 | 182 | 0.00 | Liquid | −10 | 0.062 | 2.9 |
| Com. Ex. 10 | 180 | 0.00 | Liquid | 5 | — | 9.5 |

Ester Structural Formula of Example 1:

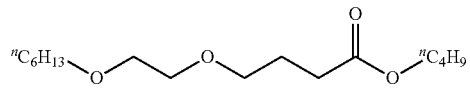

Ester Structural Formula of Example 2:

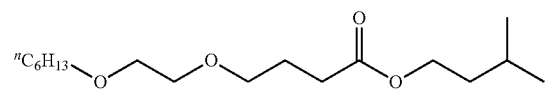

Ester Structural Formula of Example 3:

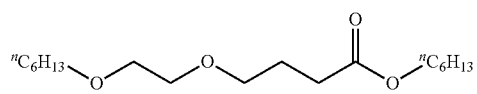

Ester Structural Formula of Example 4:

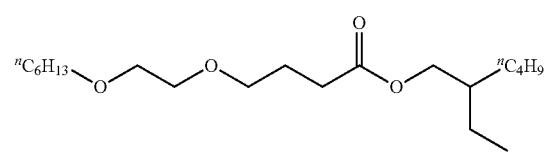

Ester Structural Formula of Example 5:

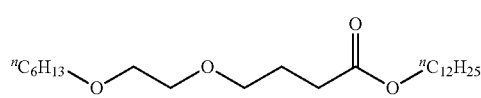

Ester Structural Formula of Example 6:

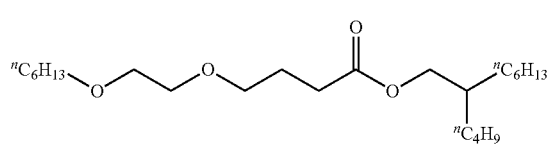

Ester Structural Formula of Example 7:

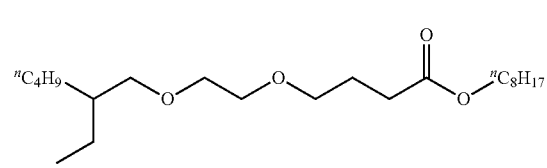

Ester Structural Formula of Example 8:

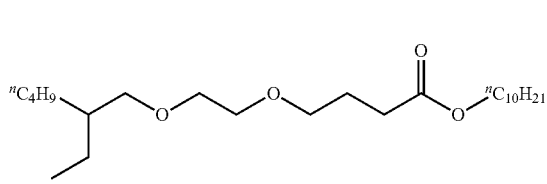

Ester Structural Formula of Example 9:

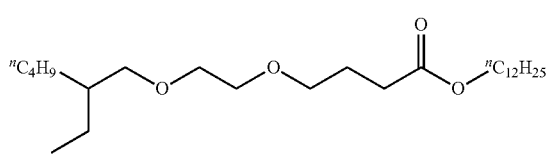

Ester Structural Formula of Example 10:

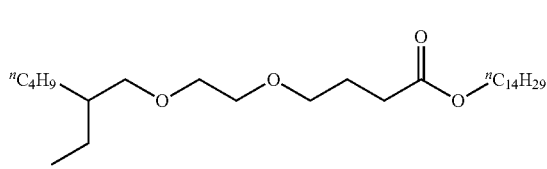

Ester Structural Formula of Example 11:

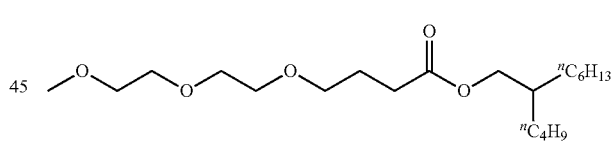

Ester Structural Formula of Example 12:

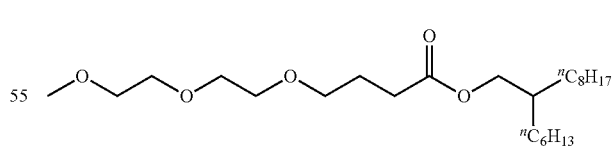

Ester Structural Formula of Example 13:

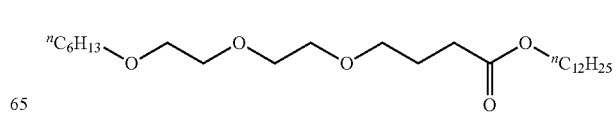

Ester Structural Formula of Example 14:

$^nC_4H_9$—O—⁀—O—⁀—O—⁀—C(=O)—O—$^nC_{10}H_{21}$

Ester Structural Formula of Example 15:

$^nC_4H_9$—O—⁀—O—⁀—O—⁀—C(=O)—O—$^nC_{12}H_{25}$

Ester Structural Formula of Example 16:

$^nC_4H_9$—O—⁀—O—⁀—O—⁀—C(=O)—O—$^nC_{14}H_{29}$

Ester Structural Formula of Example 17:

$^nC_4H_9$—O—⁀—O—⁀—O—⁀—C(=O)—O—CH($^nC_4H_9$)—

Ester Structural Formula of Example 18:

$^nC_4H_9$—O—⁀—O—⁀—O—⁀—C(=O)—O—CH($^nC_6H_{13}$)($^nC_4H_9$)

Ester Structural Formula of Comparative Example 1:

$^nC_{15}H_{31}$—C(=O)—O—CH$_3$

Ester Structural Formula of Comparative Example 2:

$^nC_{17}H_{35}$—C(=O)—O—C$_2$H$_5$

Ester Structural Formula of Comparative Example 3:

$^nC_{11}H_{23}$—C(=O)—O—$^nC_{10}H_{21}$

Ester Structural Formula of Comparative Example 4:

$^nC_{17}H_{35}$—C(=O)—O—CH$_2$CH(CH$_3$)$_2$

Ester Structural Formula of Comparative Example 5:

CH$_3$(CH$_2$)$_3$CH(C$_2$H$_5$)—C(=O)—O—$^nC_{16}H_{33}$

Ester Structural Formula of Comparative Example 6:

$^nC_{15}H_{31}$—C(=O)—O—CH$_2$CH(C$_2$H$_5$)(C$_4$H$_9$)

Ester Structural Formula of Comparative Example 7:

(2-ethylhexyl)—O—C(=O)—(CH$_2$)$_4$—C(=O)—O—(2-ethylhexyl)

Ester Structural Formula of Comparative Example 8:

(2-ethylhexyl)—O—C(=O)—(CH$_2$)$_8$—C(=O)—O—(2-ethylhexyl)

Ester Structural Formula of Comparative Example 9:

$^nC_{10}H_{21}$—C(=O)—O—CH$_2$CH(CH$_3$)CH$_2$—O—C(=O)—$^nC_{10}H_{21}$

Ester Structural Formula of Comparative Example 10:

$^nC_9H_{19}$—O—⁀—C(=O)—O—$^nC_{12}H_{25}$

As shown in Table 2, the compounds of Examples 1 through 18 were liquid at 20° C. The compounds of Examples 1 through 18 had lower solidification temperatures, as compared to existing monoesters of Comparative Examples 1 through 6 each of which existing monoesters contains no ether oxygen atom at a carboxylic site that constitutes ester. This demonstrated that the compounds of Examples 1 through 18 had excellent low-temperature fluidities as compared to the existing monoesters.

The compounds of Examples 7 and 11 had remarkably lower viscosities regardless of having larger molecular weights, as compared to the monoesters of Comparative Examples 3 through 6 and the compound of Comparative Example 7 which has been widely used as a lubricant and a plasticizer. The compounds of Examples 7 and 11 had heat resistances equal to that of the compound of Comparative Example 7. This demonstrated that the compounds of Examples 7 and 11 had remarkably excellent energy-savings and favorable heat resistances.

The compounds of Examples 8 through 10, 13 through 15, and 18 had lower viscosities regardless of having larger molecular weights, as compared to the compound of Comparative Example 8 which has been widely used as a lubricant and a plasticizer. The compounds of Examples 9, 10, 13 through 15, and 18 had lower viscosities and more excellent heat resistances as compared to the compound of Comparative Example 8. This demonstrated that the compounds of Examples 9, 10, 13 through 15, and 18 had remarkably excellent energy-savings and heat resistances. The compounds of Examples 5, 7, 9, 13 15 and 18 had friction coefficients equal to or slightly lower than those of the compounds of Comparative Examples 7 and 9. This demonstrated that the compounds of Examples 5, 7, 9, 13 15 and 18 had favorable lubricities.

The compound of Comparative Example 9 had (i) a low viscosity regardless of having a large molecular weight and (ii) an excellent heat resistance, but had a slightly poor low-temperature fluidity. The compound of Comparative Example 9 was therefore poor in balance among energy-saving, the heat resistance, and the low-temperature fluidity. It is difficult to put the compound of Comparative Example 9 into practical use. On the other hand, the compound of Example 15 had a viscosity lower than that of the compound of Comparative Example 9 though the compound of Example 15 had a molecular weight larger than that of the compound of Comparative Example 9. The compound of Example 15 was also excellent in heat resistance and low-temperature fluidity. The compound of Example 15 was thus excellent in balance among energy-saving, the heat resistance and the low-temperature fluidity, and therefore suitable for practical use.

The compound of Comparative Example 10 had (i) a low viscosity regardless of having a large molecular weight and (ii) a favorable heat resistance, but had a poor low-temperature fluidity. The compound of Comparative Example 10 was therefore poor in balance among energy-saving, the heat resistance, and the low-temperature fluidity. It is difficult to put the compound of Comparative Example 10 into practical use. On the other hand, the compound of Example 5 had a viscosity lower than that of the compound of Comparative Example 10 though the compound of Example 5 had a molecular weight equal to that of the compound of Comparative Example 10. The compound of Example 5 was also excellent in heat resistance and low-temperature fluidity. The compound of Example 5 was thus excellent in balance among energy-saving, the heat resistance and the low-temperature fluidity, and therefore suitable for practical use.

INDUSTRIAL APPLICABILITY

As compared to compounds traditionally used as lubrication oils etc., the compound of the present invention is excellent in energy-saving, heat resistance, and low-temperature fluidity, and excellent in balance among these properties. The compound of the present invention is therefore suitably usable as not only a lubricant but also a lubricant for a fluid dynamic bearing, a lubricant for a typical bearing, a lubricant for an impregnated bearing, a base oil for grease, a freezer oil, a plasticizer, and the like. As such, the present invention is remarkably high in industrial use value in all technical fields where lubricants are used.

The invention claimed is:

1. A compound being represented by the following general formula (1):

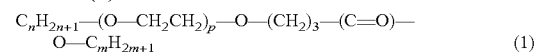

$$C_nH_{2n+1}-(O-CH_2CH_2)_p-O-(CH_2)_3-(C=O)-O-C_mH_{2m+1} \quad (1)$$

wherein O represents an oxygen atom, C represents a carbon atom, H represents a hydrogen atom, m is an integer of 10 to 14, n is an integer of 4 to 8, p is an integer of 2 to 3, and 14≤n+m≤22 is satisfied;

wherein the compound has:
a 40° C. kinetic viscosity (v) that satisfies 4 mm²/s v 30 mm²/s;
a viscosity index of not less than 160;
a solidification temperature of not higher than −10° C.;
an amount of evaporation of not more than 20 wt %; and
an acid value of not more than 1 mg KOH/g.

2. The compound as set forth in claim 1, wherein in the general formula (1), p is 2, and
the 40° C. kinetic viscosity (v) satisfies 4 mm²/s≤v≤20 mm²/s.

3. The compound as set forth in claim 1, wherein in the general formula (1), p is 3.

4. The compound as set forth in claim 1, wherein m, n and p are 12, 8, and 2, respectively, in the general formula (1).

5. The compound as set forth in claim 1, wherein m, n and p are 14, 8, and 2, respectively, in the general formula (1).

6. The compound as set forth in claim 1, wherein m, n and p are 10, 8, and 2, respectively, in the general formula (1).

7. A lubricant comprising a compound as set forth in claim 1.

8. The lubricant as set forth in claim 7, which is a lubricant for a fluid dynamic bearing or a lubricant for an impregnated bearing.

9. A bearing which is lubricated with use of a lubricant as set forth in claim 7.

10. The bearing as set forth in claim 9, which is a fluid dynamic bearing or an impregnated bearing.

11. A method of lubricating a bearing, comprising the step of lubricating the bearing with use of a lubricant as set forth in claim 7.

12. A motor comprising a bearing as set forth in claim 9.

13. A method of producing a grease, using a lubricant as set forth in claim 7.

14. A grease comprising a lubricant as set forth in claim 7.

15. A freezer oil comprising a compound as set forth in claim 1.

* * * * *